United States Patent
Li et al.

(10) Patent No.: US 12,263,038 B2
(45) Date of Patent: Apr. 1, 2025

(54) ELASTICITY IMAGING METHODS AND DEVICES, AND STORAGE MEDIUM

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventors: Shuangshuang Li, Shenzhen (CN); Donghai Qin, Shenzhen (CN); Zebing Wang, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 520 days.

(21) Appl. No.: 17/187,493

(22) Filed: Feb. 26, 2021

(65) Prior Publication Data
US 2021/0196236 A1 Jul. 1, 2021

Related U.S. Application Data

(63) Continuation of application No. PCT/CN2018/107414, filed on Sep. 25, 2018.

(51) Int. Cl.
*A61B 8/08* (2006.01)
*A61B 8/00* (2006.01)

(52) U.S. Cl.
CPC .............. *A61B 8/485* (2013.01); *A61B 8/461* (2013.01); *A61B 8/5223* (2013.01);
(Continued)

(58) Field of Classification Search
CPC ....... A61B 8/485; A61B 8/461; A61B 8/5223; A61B 8/5269; A61B 8/5284; A61B 8/543; A61B 8/56
See application file for complete search history.

(56) References Cited

U.S. PATENT DOCUMENTS 7,708,692 B2 * 5/2010 Kato .................... A61B 8/0858
600/449
9,345,451 B2 5/2016 Lee et al.
(Continued)

FOREIGN PATENT DOCUMENTS

CN 101166474 A 4/2008
CN 101317774 A 12/2008
(Continued)

OTHER PUBLICATIONS

PCT International Preliminary Report on Patentability mailed Apr. 8, 2021, issued in related International Application No. PCT/CN2018/107414, with English translation (12 pages).
(Continued)

*Primary Examiner* — Sean A Frith
(74) *Attorney, Agent, or Firm* — Sheppard Mullin Richter & Hampton LLP

(57) ABSTRACT

An elasticity imaging method, device, and storage medium are provided. The method includes: transmitting an ultrasound wave to a target tissue; receiving an ultrasound echo of the ultrasound wave returned from the target tissue; obtaining an interference characteristic information representing the degree of interference to the target tissue; and when the interference characteristic information does not meet a preset condition, stopping determining an elasticity image of the target tissue according to the ultrasound echo.

20 Claims, 6 Drawing Sheets

(52) U.S. Cl.
CPC .......... *A61B 8/5269* (2013.01); *A61B 8/5284* (2013.01); *A61B 8/543* (2013.01); *A61B 8/56* (2013.01)

(56) References Cited

U.S. PATENT DOCUMENTS

| | | | |
|---|---|---|---|
| 9,895,137 B2 | 2/2018 | Tabaru et al. | |
| 10,996,333 B2 | 5/2021 | Van Rens et al. | |
| 2008/0071174 A1* | 3/2008 | Waki | G16H 50/30 600/442 |
| 2009/0149752 A1 | 6/2009 | Osaka et al. | |
| 2010/0081937 A1* | 4/2010 | Hamilton | A61B 8/485 600/509 |
| 2011/0054321 A1 | 3/2011 | White et al. | |
| 2013/0028536 A1 | 1/2013 | Hazard | |
| 2014/0221825 A1* | 8/2014 | Mahfouz | A61B 8/14 600/443 |
| 2014/0357995 A1* | 12/2014 | Brumfield | A61B 5/7282 600/480 |
| 2015/0216446 A1* | 8/2015 | Bukhman | A61B 5/062 600/521 |
| 2016/0074674 A1* | 3/2016 | Kohli | A61B 5/0036 600/484 |
| 2017/0086792 A1* | 3/2017 | Chono | A61B 8/06 |
| 2018/0368809 A1* | 12/2018 | Mao | A61B 8/4494 |
| 2019/0254639 A1 | 8/2019 | Yin et al. | |

FOREIGN PATENT DOCUMENTS

| | | | |
|---|---|---|---|
| CN | 101869485 A | 10/2010 | |
| CN | 104302233 A | 1/2015 | |
| CN | 105310727 A | 2/2016 | |
| CN | 106154251 A | 11/2016 | |
| CN | 108351411 A | 7/2018 | |
| JP | 3932485 B2 * | 6/2007 | .......... A61B 5/0048 |
| JP | 2012-213545 A | 11/2012 | |
| KR | 10-2014-0045189 A | 4/2014 | |
| WO | 2018-082458 A1 | 5/2018 | |

OTHER PUBLICATIONS

First Search dated Aug. 26, 2021, issued in related Chinese Application No. 201880016744.9 (3 pages).
PCT International Search Report and the Written Opinion mailed Jun. 28, 2019, issued in related International Application No. PCT/CN2018/107414, with partial English translation (10 pages).

* cited by examiner

Transmitting and receiving sequence of elasticity imaging

Vibration Waveform

Ultrasound pulse for
generating the acoustic
radiation force

ELASTICITY IMAGING METHODS AND DEVICES, AND STORAGE MEDIUM

CROSS-REFERENCE TO RELATED APPLICATION

This application is a continuation application of International Patent Application No. PCT/CN2018/107414, filed on Sep. 25, 2018. The entire content of the above-identified application is incorporated herein by reference.

TECHNICAL FIELD

The present disclosure relates to elasticity imaging, in particular to an elasticity imaging method and device, and a storage medium thereof.

BACKGROUND

Elasticity imaging is a technique for representing the degree of the tissue elasticity or hardness. It is widely used in auxiliary detection, judgment of benign and malignant, and recovery after cure, etc. of a tissue cancer.

Currently, based on the principle of the elasticity imaging, the elasticity imaging method can be divided into two categories: strain-type elasticity imaging method and shear-wave elasticity imaging method. In the strain-type elasticity imaging method, the imaging is mainly performed by producing a certain deformation in the tissue. In the shear-wave elasticity imaging, the imaging is mainly performed by generating a shear wave inside the tissue. The shear-wave elasticity imaging method may be further divided into two categories: the shear-wave elasticity imaging method in which the shear wave is generated by an acoustic radiation force, and the transient elasticity imaging method in which the shear wave is generated by an external vibration.

During the actual clinical examination, it is difficult to completely stop the motion of the examination object, such as the heartbeat, the blood vessel pulse, the breathing or the like. For the strain-type elasticity imaging method, the motion interference will cause uneven pressure applied by the probe, which results in inaccurate imaging. For the shear-wave elasticity imaging method, the motion interference will easily lead to inaccurate capture of the shear wave signals, which also results in inaccurate imaging.

SUMMARY

In one embodiment of the present disclosure, elasticity imaging methods, devices and storage medium are provided, in which whether to obtain the elasticity image of the target tissue may be determined according to the interference characteristic information that represents the degree of interference to the target tissue, thereby improving the accuracy of the elasticity image.

In one embodiment, an elasticity imaging method is provided, which may include: transmitting an ultrasound wave to a target tissue; receiving an ultrasound echo of the ultrasound wave returned from the target tissue; obtaining an interference characteristic information, where the interference characteristic information represents a degree of interference to the target tissue; and when the interference characteristic information does not meet a preset condition, stopping obtaining an elasticity image of the target tissue according to the ultrasound echo.

In one embodiment, an elasticity imaging method is provided, which may include: obtaining an interference characteristic information, where the interference characteristic information represents a degree of interference to a target tissue; when the interference characteristic information meets a preset condition, transmitting an ultrasound wave to the target tissue; receiving an ultrasound echo of the ultrasound wave returned from the target tissue; obtaining an elasticity image of the target tissue according to the ultrasound echo; and displaying the elasticity image.

In one embodiment, an elasticity imaging method is provided, which may include: performing an elasticity imaging on a target tissue to obtain an elasticity image of the target tissue; obtaining an interference characteristic information, where the interference characteristic information represents a degree of interference to the target tissue; when the interference characteristic information does not meet a preset condition, stopping displaying the elasticity image.

In one embodiment, an elasticity imaging device is provided, which may include a processor, a memory, a communication bus, a display and an ultrasound probe.

The communication bus is configured to implement a communication connection between the processor, the memory, the display and the ultrasound probe.

The processor is configured to execute an elasticity imaging program stored in the memory to: control the ultrasound probe to transmit an ultrasound wave to a target tissue; receive an ultrasound echo of the ultrasound wave returned from the target tissue through the ultrasound probe; obtain an interference characteristic information, where the interference characteristic information represents a degree of interference to the target tissue; and when the interference characteristic information does not meet a preset condition, stop obtaining an elasticity image of the target tissue according to the ultrasound echo.

The display is configured to display the elasticity image.

In one embodiment, an elasticity imaging device is provided, which may include a processor, a memory, a communication bus, a display and an ultrasound probe.

The communication bus is configured to implement a communication connection between the processor, the memory, the display and the ultrasound probe.

The processor is configured to execute an elasticity imaging program stored in the memory to: obtain an interference characteristic information, where the interference characteristic information represents a degree of interference to a target tissue; when the interference characteristic information meets a preset condition, control the ultrasound probe to transmit an ultrasound wave to the target tissue; receive an ultrasound echo of the ultrasound wave returned from the target tissue through the ultrasound probe; and obtain an elasticity image of the target tissue according to the ultrasound echo.

The display is configured to display the elasticity image.

In one embodiment, an elasticity imaging device is provided, which may include a processor, a memory, a communication bus, a display and an ultrasound probe.

The communication bus is configured to implement a communication connection between the processor, the memory, the display and the ultrasound probe.

The processor is configured to execute an elasticity imaging program stored in the memory to: perform an elasticity imaging on a target tissue through the ultrasound probe to obtain an elasticity image of the target tissue, and obtain an interference characteristic information, where the interference characteristic information represents a degree of interference to the target tissue.

The display is configured to stop displaying the elasticity image when the interference characteristic information does not meet a preset condition.

In one embodiment, a computer-readable storage medium storing an elasticity imaging program is provided. The elasticity imaging program is able to be executed by a processor to implement the elasticity imaging methods above.

In the technical solutions of the embodiments of the present disclosure, the ultrasound waves may be transmitted to the target tissue; the ultrasound echoes of the ultrasound waves returned from the target tissue may be received; the interference characteristic information may be obtained, where the interference characteristic information may represent the degree of interference to the target tissue; and when the interference characteristic information does not meet the preset conditions, obtaining the elasticity image of the target tissue according to the ultrasound echoes may be stopped. That is to say, in the technical solutions provided by the embodiments of the present disclosure, whether to obtain the elasticity image of the target tissue may be determined according to the interference characteristic information that represents the degree of interference to the target tissue. That is, the elasticity image can be determined when the interference to the target tissue is weak. Therefore, the accuracy of the elasticity image can be improved.

DETAILED DESCRIPTION

In order to understand the features and technical content of the embodiments of the present disclosure in more detail, the implementation of the embodiments of the present disclosure will be described in detail below with reference to the drawings. The drawings are for reference and description purposes only, but not used to limit the embodiments of the present disclosure.

Figure 1:
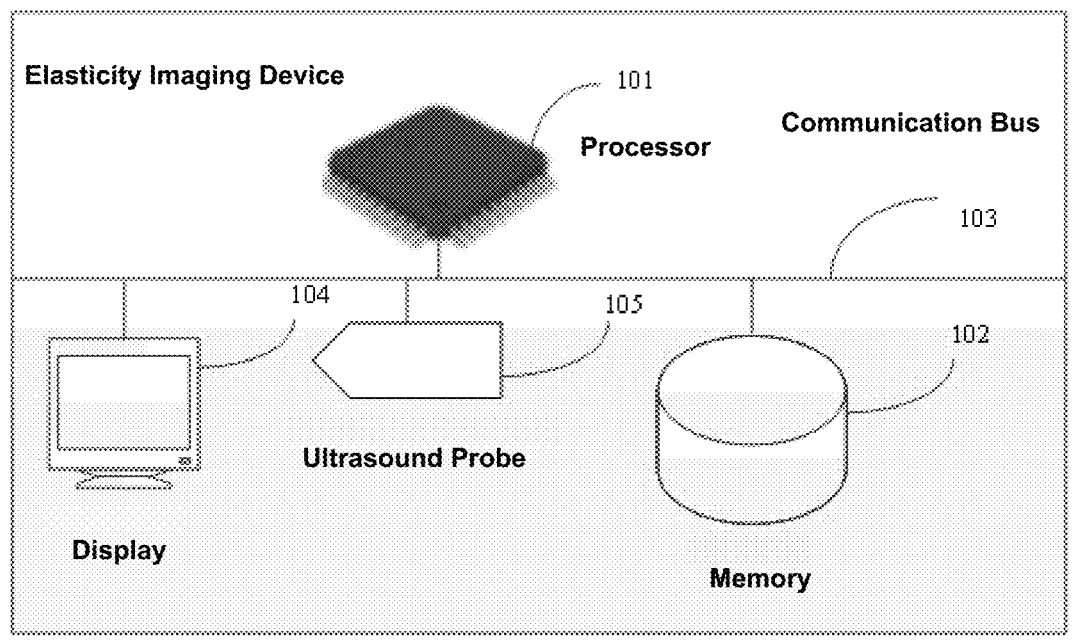
FIG. 1 is a schematic diagram of an elasticity imaging device in one embodiment of the present disclosure.

The elasticity imaging mainly refers to imaging and signal processing techniques for the purpose of representing the difference in tissue elasticity. FIG. 1 is a schematic diagram of an elasticity imaging device in one embodiment of the present disclosure. As shown in FIG. 1, the elasticity imaging device may include a processor 101, a memory 102, a communication bus 103, a display 104 and an ultrasound probe 105.

The communication bus 103 may be configured to implement the communication connection between the processor 101, the memory 102, the display 104 and the ultrasound probe 105.

The processor 101 may be configured to execute the elasticity imaging program stored in the memory 102 so as to implement the elasticity imaging method.

In one embodiment of the present disclosure, the display 104 included in the elasticity imaging device may be a touch screen, a liquid crystal display, etc., or may be an independent display device such as a liquid crystal display, a TV or the like independent of the elasticity imaging device. Alternatively, it may also be the display screen in an electronic device such as a mobile phone, a tablet computer or the like.

In one embodiment of the present disclosure, the memory 102 included in the elasticity imaging device may be a flash memory card, a solid state memory, a hard disk, or the like.

In one embodiment of the present disclosure, a computer-readable storage medium may also be provided, which may store a plurality of program instructions. The plurality of program instructions may be invoked and executed by the processor 101 to perform a part or all or any combination of the steps in the elasticity imaging methods in one embodiment of the present disclosure.

In one embodiment, the computer-readable storage medium may be the memory 102, which may be a non-volatile storage medium such as a flash memory card, a solid-state memory, a hard disk, or the like.

In one embodiment of the present disclosure, the processor 101 included in the elasticity imaging device may be implemented by software, hardware, firmware, or a combination thereof, and may use circuits, single or multiple application specific integrated circuits (ASIC), single or multiple general integrated circuits, single or multiple microprocessors, single or multiple programmable logic devices, or a combination of the foregoing circuits or devices, or other suitable circuits or devices, such that the processor 101 can execute the steps of the elasticity imaging methods in the embodiments.

The elasticity imaging methods in the present disclosure will be described in detail below based on the elasticity imaging device above.

Figure 2:
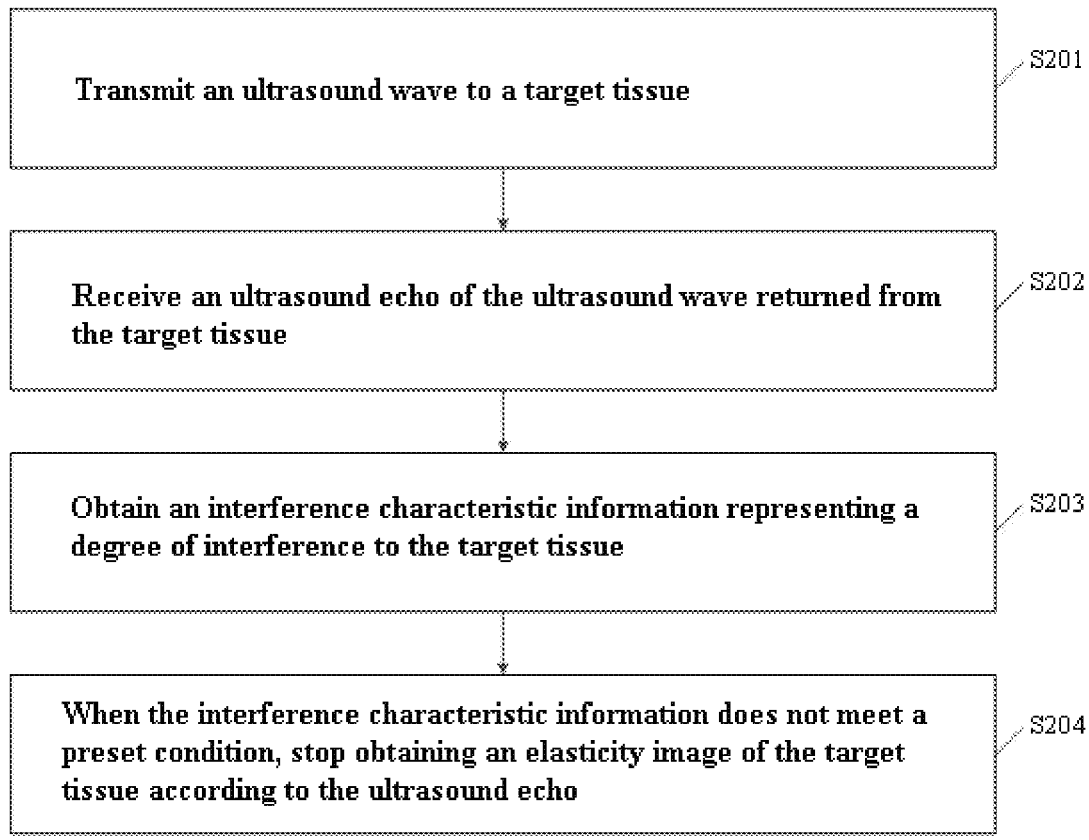
FIG. 2 is a schematic flow chart of an elasticity imaging method in one embodiment of the present disclosure.

FIG. 2 is a schematic flow chart of an elasticity imaging method in one embodiment of the present disclosure. As shown in FIG. 2, the method may include the following steps.

In step S201, the ultrasound waves may be transmitted to the target tissue.

In the embodiment of the present disclosure, the processor 101 of the elasticity imaging device may control the ultrasound probe 105 to transmit the ultrasound waves to the target tissue.

In one embodiment of the present disclosure, the processor 101 of the elasticity imaging device may control the ultrasound probe 105 to transmit the ultrasound waves to the target tissue in a specific way, which will not be limited herein.

It can be understood that, in one embodiment of the present disclosure, the elasticity imaging method may be used to obtain an elasticity image that represents the degree of elasticity of the target tissue. The target tissue may be a part of the human body, which will not be limited herein.

In step S202, the ultrasound echoes of the ultrasound waves returned from the target tissue may be received.

In one embodiment of the present disclosure, after the processor 101 of the elasticity imaging device controls the ultrasound probe 105 to transmit the ultrasound waves to the target tissue, the ultrasound waves will be reflected when reaching the target tissue. Therefore, the ultrasound probe 105 of the elasticity imaging device may receive the ultrasound echoes of the ultrasound waves returned from the target tissue.

Figure 3:
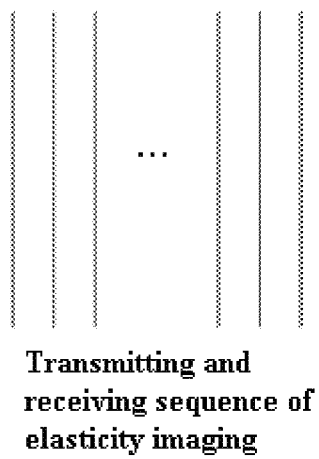
FIG. 3 is a schematic diagram of an exemplary transmitting and receiving sequence of an ultrasound probe in one embodiment of the present disclosure.

FIG. 3 is a schematic diagram of an exemplary transmitting and receiving sequence of the ultrasound probe in one embodiment of the present disclosure. As shown in FIG. 3, the processor 101 of the elasticity imaging device may use the elasticity imaging transmitting and receiving sequence shown in FIG. 3 to control the ultrasound probe 105 to transmit the ultrasound waves and receive the ultrasound echoes.

In one embodiment of the present disclosure, the processor 101 of the elasticity imaging device may obtain the elasticity image of the target tissue according to the ultrasound echoes.

In step S203, the interference characteristic information may be obtained. The interference characteristic information may represent the degree of interference to the target tissue.

In one embodiment of the present disclosure, the processor 101 of the elasticity imaging device may obtain the interference characteristic information.

In one embodiment of the present disclosure, the processor 101 of the elasticity imaging device may obtain the interference characteristic information at any time or in any time period within the time from the ultrasound probe 105 transmitting the ultrasound waves to the target tissue to receiving the ultrasound echoes, which will not be limited herein.

In one embodiment of the present disclosure, the interference characteristic information may represent the degree of interference to the target tissue. The interference characteristic information may include at least one of the amplitude value of the ECG signal, the amplitude value of the respiratory wave signal and the displacement value of the target tissue, which will not be limited herein.

In one embodiment of the present disclosure, the processor 101 of the elasticity imaging device may obtain different interference characteristic information in different ways.

In one embodiment, the interference characteristic information may be the amplitude value of the ECG signal. The processor 101 of the elasticity imaging device may obtain the ECG signal through electrodes so as to extract the amplitude value of the ECG signal. This way, the interference characteristic information may be obtained.

In one embodiment, the interference characteristic information may be the amplitude value of the respiratory wave signal. The processor 101 of the elasticity imaging device may obtain the respiratory wave signal through an electrode, so as to extract the amplitude value of the respiratory wave signal. This way, the interference characteristic information may be obtained.

In one embodiment, the interference characteristic information may be the displacement value of the target tissue. The processor 101 of the elasticity imaging device may obtain the interference characteristic information by obtaining a first ultrasound data of the target tissue at a first time, obtaining a first position information of the target tissue according to the first ultrasound data, obtaining a second ultrasound data of the target tissue at a second time, obtaining a second position information of the target tissue according to the second ultrasound data, and obtaining the displacement value of the target tissue according to the first position information and the second position information.

In one embodiment of the present disclosure, the processor 101 of the elasticity imaging device may control the ultrasound probe 105 to transmit a series of ultrasound waves for determining the position of the target tissue to the target tissue at the first time and the second time, so as to obtain the first ultrasound data and the second ultrasound data and further obtain the displacement value of the target tissue according to the first ultrasound data and the second ultrasound data.

In one embodiment of the present disclosure, the ultrasound waves for determining the position of the target tissue may be customized ultrasound waves or the ultrasound waves for conventional ultrasound B imaging, which will not be limited herein.

In step S204, when the interference characteristic information does not meet a preset condition, obtaining the elasticity image of the target tissue according to the ultrasound echoes may be stopped.

In one embodiment of the present disclosure, the processor 101 of the elasticity imaging device may determine whether the interference characteristic information meets the preset condition after obtaining the interference characteristic information, and, when the interference characteristic information does not meet the preset condition, stop obtaining the elasticity image of the target tissue according to the ultrasound echoes.

In one embodiment of the present disclosure, after the step S203, the processor 101 of the elasticity imaging device may determine whether the interference characteristic information meets the preset condition.

Specifically, in one embodiment of the present disclosure, the interference characteristic information may be the amplitude value of the ECG signal, and determining whether the interference characteristic information meet the preset condition after the processor 101 of the elasticity imaging device obtains the interference characteristic information may include the following ways.

It may be determined whether the amplitude value of the ECG signal is not greater than a first preset threshold. When it is greater than the first preset threshold, obtaining the elasticity image of the target tissue according to the ultrasound echoes may be stopped.

Alternatively, it may be determined whether the amplitude value of the ECG signal is not greater than the first preset threshold and not less than a second preset threshold. When it is greater than the first preset threshold or less than the second preset threshold, obtaining the elasticity image of the target tissue according to the ultrasound echoes may be stopped.

Alternatively, the maximum amplitude value of the ECG signal may be obtained from the amplitude values of the ECG signal, and it may be determined whether the maximum amplitude value of the ECG signal is not greater than a third preset threshold. When the maximum amplitude value of the ECG signal is greater than the third preset threshold, obtaining the elasticity image of the target tissue according to the ultrasound echoes may be stopped.

Alternatively, the maximum difference value of the amplitude values of the ECG signal may be determined according to the amplitude values of the ECG signal. It may be determined whether the maximum difference value of the amplitude values of the ECG signal is not greater than a fourth preset threshold. When the maximum difference value of the amplitude values of the ECG signal is greater than the fourth preset threshold, obtaining the elasticity image of the target tissue according to the ultrasound echoes may be stopped.

Alternatively, the maximum amplitude value of the ECG signal may be determined from the amplitude values of the ECG signal, and a first time corresponding to the maximum amplitude value of the ECG signal may be determined. Obtaining the elasticity image of the target tissue according to the ultrasound echoes may be stopped at a second time that is at a preset time interval from the first time.

In one embodiment of the present disclosure, the memory 102 of the elasticity imaging device may store the preset time interval, the first preset threshold, the second preset threshold, the third preset threshold and the fourth preset threshold. The preset time interval, the first preset threshold, the second preset threshold, the third preset threshold and the fourth preset threshold may be set by the user based on experience or actual needs, which will not be limited herein.

In one embodiment, the interference characteristic information is the amplitude value of the ECG signal. The amplitude value of the ECG signal obtained by the processor 101 of the elasticity imaging device is X1, and the first preset threshold is Y1. When X1 is greater than Y1, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the ECG signal. The amplitude value of the ECG signal obtained by the processor 101 of the elasticity imaging device is X2, the first preset threshold is Y1, and the second preset threshold is Y2. When X2 is greater than Y1 or X2 is less than Y2, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the ECG signal. The processor 101 of the elasticity imaging device may obtain the amplitude values of the ECG signal within a period of time, and determine therefrom that the maximum amplitude value of the ECG signal is X3. The third preset threshold is Y3. When X3 is greater than Y3, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the ECG signal. The processor 101 of the elasticity imaging device may obtain the amplitude values of the ECG signal within a period of time, and determines that the maximum difference value of the amplitude values of the ECG signal is X4. The fourth preset threshold is Y4. When X4 is greater than Y4, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the ECG signal. The processor 101 of the elasticity imaging device may obtain the amplitude values of the ECG signal within a period of time, select the maximum amplitude value of the ECG signal therefrom, and further determine the first time corresponding to maximum amplitude value of the ECG signal as t1. The preset time interval is t. At a second time t2 that is at an interval of t from t1, the interference characteristic information does not meet the preset conditions. In this case, the processor 101 of the elasticity imaging device may stop obtaining the elasticity image of the target tissue according to the ultrasound echoes.

Specifically, in one embodiments of the present disclosure, the interference characteristic information may be the amplitude value of the respiratory wave signal, and determining whether the interference characteristic information meet the preset condition after the processor 101 of the elasticity imaging device obtains the interference characteristic information may include the following ways.

It may be determined whether the amplitude value of the respiratory wave signal is not greater than a first preset threshold. When it is greater than the first preset threshold, obtaining the elasticity image of the target tissue according to the ultrasound echoes may be stopped.

Alternatively, it may be determined whether the amplitude value of the respiratory wave signal is not greater than the first preset threshold and not less than a second preset threshold. When it is greater than the first preset threshold or less than the second preset threshold, obtaining the elasticity image of the target tissue according to the ultrasound echoes may be stopped.

Alternatively, the maximum amplitude value of the respiratory wave signal may be obtained from the amplitude values of the respiratory wave signal, and it may be determined whether the maximum amplitude value of the respiratory wave signal is not greater than a third preset threshold. When the maximum amplitude value of the respiratory wave signal is greater than the third preset threshold, obtaining the elasticity image of the target tissue according to the ultrasound echoes may be stopped.

Alternatively, the maximum difference value of the amplitude values of the respiratory wave signal may be determined according to the amplitude values of the respiratory wave signal. It may be determined whether the maximum difference value of the amplitude values of the respiratory wave signal is not greater than a fourth preset threshold. When the maximum difference value of the amplitude values of the respiratory wave signal is greater than the fourth preset threshold, obtaining the elasticity image of the target tissue according to the ultrasound echoes may be stopped.

Alternatively, the maximum amplitude value of the respiratory wave signal may be determined from the amplitude values of the respiratory wave signal, and a first time corresponding to the maximum amplitude value of the respiratory wave signal may be determined. Obtaining the elasticity image of the target tissue according to the ultrasound echoes may be stopped at a second time that is at a preset time interval from the first time.

In one embodiment, the interference characteristic information is the amplitude value of the respiratory wave signal. The amplitude value of the respiratory wave signal obtained by the processor 101 of the elasticity imaging device is M1, and the first preset threshold is Y1. When M1 is greater than Y1, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the respiratory wave signal. The amplitude value of the respiratory wave signal obtained by the processor 101 of the elasticity imaging device is M2, the first preset threshold is Y1, and the second preset threshold is Y2. When M2 is greater than Y1 or M2 is less than Y2, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the respiratory wave signal. The processor 101 of the elasticity imaging device may obtain the amplitude values of the respiratory wave signal within a period of time, and determine therefrom that the maximum amplitude value of the respiratory wave signal is M3. The third preset threshold is Y3. When M3 is greater than Y3, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the respiratory wave signal. The processor 101 of the elasticity imaging device may obtain the amplitude values of the respiratory wave signal within a period of time, and determines that the maximum difference value of the amplitude values of the respiratory wave signal is M4. The fourth preset threshold is Y4. When M4 is greater than Y4, the interference characteristic information does not meet the preset condition. In this case, the processor 101 of the elasticity imaging device may stop obtaining the elasticity image of the target tissue according to the ultrasound echoes.

In one embodiment, the interference characteristic information is the amplitude value of the respiratory wave signal. The processor 101 of the elasticity imaging device may obtain the amplitude values of the respiratory wave signal within a period of time, select the maximum amplitude value of the respiratory wave signal therefrom, and further determine the first time corresponding to maximum amplitude value of the respiratory wave signal as t1. The preset time interval is t. At the second time t2 that is at an interval of t from t1, the interference characteristic information does not meet the preset conditions. In this case, the processor 101 of the elasticity imaging device may stop obtaining the elasticity image of the target tissue according to the ultrasound echoes.

Specifically, in one embodiments of the present disclosure, the interference characteristic information may be the displacement value of the target tissue, and determining whether the interference characteristic information meet the preset condition after the processor 101 of the elasticity imaging device obtains the interference characteristic information may include the following ways.

It may be determined whether the displacement value of the target tissue is not greater than a first preset threshold. When it is greater than the first preset threshold, obtaining the elasticity image of the target tissue according to the ultrasound echoes may be stopped.

Alternatively, it may be determined whether the displacement value of the target tissue is not greater than a first preset threshold and not less than a second preset threshold. When it is greater than the first preset threshold or less than the second preset threshold, obtaining the elasticity image of the target tissue according to the ultrasound echoes may be stopped.

Alternatively, the maximum displacement value of the target tissue may be obtained from the displacement values of the target tissue, and it may be determined whether the maximum displacement value of the target tissue is not greater than a third preset threshold. When the maximum displacement value of the target tissue is greater than the third preset threshold, obtaining the elasticity image of the target tissue according to the ultrasound echoes may be stopped.

Alternatively, the maximum difference value of the displacement values may be determined according to the displacement values of the target tissue. It may be determined whether the maximum difference value of the displacement values is not greater than a fourth preset threshold. When the maximum difference value of the displacement values is greater than the fourth preset threshold, obtaining the elasticity image of the target tissue according to the ultrasound echoes may be stopped.

Alternatively, the maximum displacement value may be determined from the displacement values of the target tissue, and a first time corresponding to the maximum displacement value may be determined. Obtaining the elasticity image of the target tissue according to the ultrasound echoes may be stopped at a second time that is at a preset time interval from the first time.

In one embodiment, the interference characteristic information is the displacement value of the target tissue. The displacement value of the target tissue obtained by the processor 101 of the elasticity imaging device is P1, and the first preset threshold is Y1. When P1 is greater than Y1, the interference characteristic information does not meet the preset condition. In this case, the processor 101 of the elasticity imaging device may stop obtaining the elasticity image of the target tissue according to the ultrasound echoes.

In one embodiment, the interference characteristic information is the displacement value of the target tissue. The displacement value of the target tissue obtained by the processor 101 of the elasticity imaging device is P2, the first preset threshold is Y1, and the second preset threshold is Y2. When P2 is greater than Y1 or P2 is less than Y2, the interference characteristic information does not meet the preset condition. In this case, the processor 101 of the elasticity imaging device may stop obtaining the elasticity image of the target tissue according to the ultrasound echoes.

In one embodiment, the interference characteristic information is the displacement value of the target tissue. The processor 101 of the elasticity imaging device may obtain multiple displacement values of the target tissue within a period of time, and determine therefrom that the maximum displacement value is P3. The third preset threshold is Y3. When P3 is greater than Y3, the interference characteristic information does not meet the preset condition. In this case, the processor 101 of the elasticity imaging device may stop obtaining the elasticity image of the target tissue according to the ultrasound echoes.

In one embodiment, the interference characteristic information is the displacement value of the target tissue. The processor 101 of the elasticity imaging device may obtain multiple displacement values of the target tissue within a period of time, and determines that the maximum difference value of the displacement values is P4. The fourth preset threshold is Y4. When P4 is greater than Y4, the interference characteristic information does not meet the preset condition. In this case, the processor 101 of the elasticity imaging device may stop obtaining the elasticity image of the target tissue according to the ultrasound echoes.

In one embodiment, the interference characteristic information is the displacement value of the target tissue. The processor 101 of the elasticity imaging device may obtain multiple displacement values of the target tissue within a period of time, select the maximum displacement value therefrom, and further determine the first time corresponding to maximum displacement value as t1. The preset time interval is t. At a second time t2 that is at an interval of t from t1, the interference characteristic information does not meet the preset conditions. In this case, the processor 101 of the elasticity imaging device may stop obtaining the elasticity image of the target tissue according to the ultrasound echoes.

It is understandable that, in one embodiment of the present disclosure, the processor 101 of the elasticity imaging device may determine whether to stop obtaining the elasticity image according to the interference characteristic information. In other words, the degree of interference to the target tissue may be determined according to the interference characteristic information. When the interference is strong, e.g., when the amplitude of the motion of human body is large, even if the elasticity image is obtained according to the ultrasound echoes, it is inaccurate. Therefore, the obtaining of the elasticity image can be stopped.

In one embodiment of the present disclosure, after step S203, there may be a step S205.

In S205, when the interference characteristic information meets the preset condition, the elasticity image of the target tissue may be obtained according to the ultrasound echoes.

In one embodiment of the present disclosure, when the processor 101 of the elasticity imaging device determines that the interference characteristic information meets the preset condition (e.g., when the interference characteristic information is the amplitude value of the ECG signal, the processor 101 of the elasticity imaging device determines that the amplitude value of the ECG signal is not greater than the first preset threshold), the elasticity image of the target tissue may be obtained according to the ultrasound echoes.

It is understandable that, in one embodiment of the present disclosure, when the processor 101 of the elasticity imaging device determines that the interference characteristic information meets the preset condition, it means that the degree of interference to the target tissue is weak and the ultrasound echoes are obtained in a stable state of the target tissue. In this case, the elasticity image of the target tissue may be obtained according to the ultrasound echoes.

Specifically, in one embodiment of the present disclosure, the processor 101 of the elasticity imaging device obtaining the elasticity image of the target tissue according to the ultrasound echoes may include determining a deformation parameter of the target tissue according to the ultrasound echoes and obtaining the elasticity image of the target tissue according to the deformation parameter.

Specifically, in one embodiment of the present disclosure, the processor 101 of the elasticity imaging device obtaining the elasticity image of the target tissue according to the ultrasound echoes may include determining a propagation parameter of a shear wave propagating in the target tissue according to the ultrasound echoes and obtaining the elasticity image of the target tissue according to the propagation parameter.

In one embodiment of the present disclosure, the elasticity imaging method may be the strain-type elasticity imaging method or the shear-wave elasticity imaging method. The shear-wave elasticity imaging method may be the shear-wave elasticity imaging method in which the shear wave is generated based on the acoustic radiation force or the transient elasticity imaging method in which the shear wave is generated based on an external vibration. The imaging processes of different elasticity imaging methods are different. Therefore, the specific meanings of the ultrasound echoes received by the ultrasound probe 105 of the elasticity imaging device may be different. For the strain-type elasticity imaging method, the ultrasound echoes may be used to determine the deformation parameter of the target tissue. For the shear-wave elasticity imaging method, the ultrasound echoes may be used to determine the propagation parameter of the shear wave propagating in the target tissue.

In one embodiment of the present disclosure, the user may control the ultrasound probe 105 to press the target tissue, so as to deform the target tissue.

In one embodiment of the present disclosure, the processor 101 of the elasticity imaging device may control the ultrasound probe 105 to transmit ultrasound pulses that generate acoustic radiation force to the target tissue or to vibrate, so as to generate the shear wave that will propagate in the target tissue.

Figure 4:
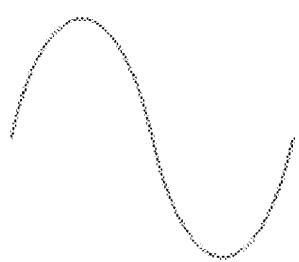
FIG. 4 is a schematic diagram of an exemplary vibration waveform in one embodiment of the present disclosure.

FIG. 4 is a schematic diagram of an exemplary vibration waveform in one embodiment of the present disclosure. As shown in FIG. 4, for the transient elasticity imaging method in which the shear wave is generated based on the external vibration, the processor 101 of the elasticity imaging device may drive the ultrasound probe 105 to vibrate as shown in FIG. 4 so as to generate the shear wave that will propagate in the target tissue.

Figure 5:
FIG. 5 is a schematic diagram of an exemplary ultrasound pulse in one embodiment of the present disclosure.

FIG. 5 is a schematic diagram of an exemplary ultrasound pulse in one embodiment of the present disclosure. As shown in FIG. 5, for the shear-wave elasticity imaging method in which the shear wave is generated based on the acoustic radiation force, the processor 101 of the elasticity imaging device may control the ultrasound probe 105 to transmit the ultrasound pulse that generates the acoustic radiation force as shown in FIG. 5 so as to generate the shear wave which will propagate in the target tissue under the action of the acoustic radiation force.

In one embodiment of the present disclosure, for the shear-wave elasticity imaging method, the sequence of generating the shear wave and detecting the propagation process of the shear wave may change. For example, in step S101, the ultrasound probe 105 of the elasticity imaging device may transmit the ultrasound waves and receive the ultrasound echoes before the shear wave is generated. In other words, it will be possible as long as the two steps of generating shear wave and detecting the propagation process of shear wave can be effectively completed.

In one embodiment of the present disclosure, after the ultrasound probe 105 of the elasticity imaging device receives the ultrasound echoes, the processor 101 may determine the tissue parameter information of the target tissue according to the ultrasound echoes, and the display 104 may display the tissue parameter information.

In one embodiment of the present disclosure, in step S201, when the processor 101 of the elasticity imaging device controls the ultrasound probe 105 to transmit the ultrasound waves, the transmitting and receiving sequence for, such as, B image, C image or M image may be used to control the transmitting of the ultrasound waves and the receiving of the ultrasound echoes. Therefore, the processor 101 of the elasticity imaging device may also determine the tissue parameter information of the target tissue such as the morphological structure or the blood flow distribution, etc. of the target tissue according to the ultrasound echoes.

In one embodiment of the present disclosure, after step S203, there may further be a step S206.

In step S206, the interference characteristic information may be displayed.

In one embodiment of the present disclosure, after the processor 101 of the elasticity imaging device obtains the interference characteristic information, the display 104 may display the interference characteristic information.

In one embodiment of the present disclosure, the display 104 of the elasticity imaging device may directly display the interference characteristic information, such as directly display the specific value of the interference characteristic information or display the interference characteristic information in the form of a list, which will not be limited herein.

Specifically, in one embodiment of the present disclosure, the processor 101 of the elasticity imaging device may generate an interference characteristic image according to the interference characteristic information, and the display 104 may display the interference characteristic image.

Figure 6:
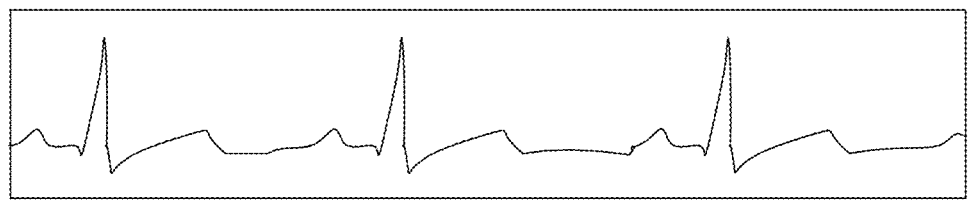
FIG. 6 is an exemplary schematic diagram showing the interference characteristic information in one embodiment of the present disclosure.

FIG. 6 is an exemplary schematic diagram for displaying the interference characteristic information in one embodiment of the present disclosure. As shown in FIG. 6, the interference characteristic information is the amplitude value of the ECG signal, and the processor 101 of the elasticity imaging device may generate the interference characteristic image, that is, the ECG waveform, according to the amplitude value of the ECG signal. The display 104 of the elasticity imaging device may display the ECG waveform.

Figure 7:
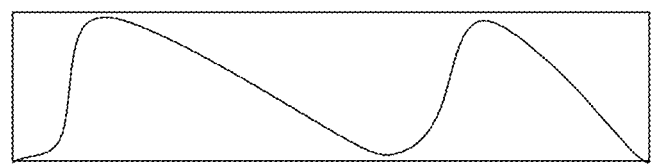
FIG. 7 is an exemplary schematic diagram showing the interference characteristic information in one embodiment of the present disclosure.

FIG. 7 is an exemplary schematic diagram for displaying the interference characteristic information in one embodiment of the present disclosure. As shown in FIG. 7, the interference characteristic information is the amplitude value of the respiratory wave signal, and the processor 101 of the elasticity imaging device may generate the interference characteristic image, that is, the respiratory waveform, according to the amplitude value of the respiratory wave signal. The display 104 of the elasticity imaging device may display the respiratory waveform.

In one embodiment of the present disclosure, after step S206, there may further be a step S207 or S208.

In step S207, a first control instruction may be received. The first control instruction may instruct to stop obtaining the elasticity image of the target tissue according to the ultrasound echoes.

In one embodiment of the present disclosure, after the display 104 of the elasticity imaging device displays the interference characteristic information, the processor 101 may receive the first control instruction which instructs to stop obtaining the elasticity image of the target tissue according to the ultrasound echoes It is understandable that, in one embodiment of the present disclosure, the memory 102 of the elasticity imaging device may also pre-store a corresponding standard value for the user to view so as to compare it with the displayed interference characteristic information to determine whether to send the corresponding control instructions to the elasticity imaging device.

In step S208, a second control instruction may be received. The second control instruction may instruct to obtain the elasticity image of the target tissue according to the ultrasound echoes.

In one embodiment of the present disclosure, after the display 104 of the elasticity imaging device displays the interference characteristic information, the second control instruction instructing to obtain the elasticity image of the target tissue according to the ultrasound echoes may be received.

In one embodiment of the present disclosure, the first control instruction and the second control instruction may be inputted to the processor 101 of the elasticity imaging device by the user through a button or a touch interface on the elasticity imaging device based on the interference characteristic information displayed on the display 104 of the elasticity imaging device.

It is understandable that, in one embodiment of the present disclosure, the user may autonomously determine whether it is currently suitable to obtain the elasticity image of the target tissue according to the ultrasound echoes based on the interference characteristic information displayed on the display 104 of the elasticity imaging device. For example, when the interference characteristic information is the amplitude value of the ECG signal, when the user sees that the amplitude value of the ECG signal fluctuates sharply, it can be determined that the target tissue is currently in a non-stationary state. At this time, if the elasticity image is obtained according to the ultrasound echoes, the obtained elasticity image will be inaccurate. Therefore, the user can input the first control instruction to the elasticity imaging device. When the user sees that the amplitude value of the ECG signal fluctuates relatively smoothly, it can be determined that the target tissue is currently in a stable state. At this time, if the elasticity image is obtained according to the ultrasound echoes, the obtained elasticity image will be accurate. Therefore, the user can input the second control instruction to the elasticity imaging device.

Figure 8:
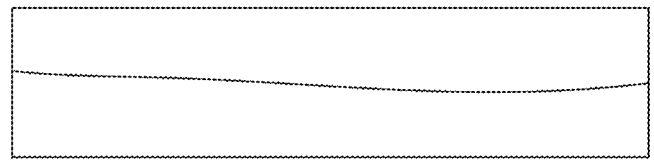
FIG. 8 is an exemplary schematic diagram showing the interference characteristic information in one embodiment of the present disclosure.

FIG. 8 is an exemplary schematic diagram for displaying the interference characteristic information in one embodiment of the present disclosure. As shown in FIG. 8, the interference characteristic information is the amplitude value of the respiratory wave signal. When the breath is held, the amplitude value of the respiratory wave signal changes smoothly, and the respiratory waveform is relatively stable. At this time, the target tissue is in a stable state. Therefore, the user can input the second control instruction through the user interface of the elasticity imaging device to instruct to obtain the elasticity image of the target tissue according to the ultrasound echoes.

In one embodiment of the present disclosure, the processor 101 of the elasticity imaging device may also determine the start time and the end time corresponding to the elasticity image, and mark the start time and the end time.

In one embodiment of the present disclosure, the processor 101 of the elasticity imaging device may mark the start time and the end time corresponding to the elasticity image in different ways. For example, the start time and the end time may be marked on the interference characteristic information displayed on the display 104, or be marked on the interface of the displayed elasticity image. In addition, different colors or different shapes (such as vertical lines, small triangles, etc.) may also be used to mark the start time and the end time. The ways for marking the start time and the end time will not be limited herein.

Figure 9:
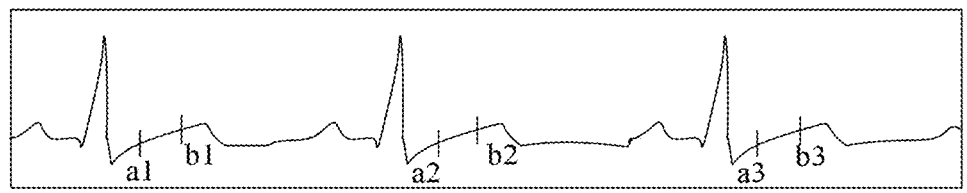
FIG. 9 is an exemplary schematic diagram in which a start time and an end time are marked in one embodiment of the present disclosure.

FIG. 9 is an exemplary schematic diagram showing the marking of the start time and the end time in one embodiment of the present disclosure. As shown in FIG. 9, the start time and end time for performing the elasticity imaging are marked on the ECG waveform formed by the amplitude values of the ECG signal displayed on the display 104, where a1, a2 and a3 represent the start times, and B1, b2 and b3 represent the end times.

Figure 10:
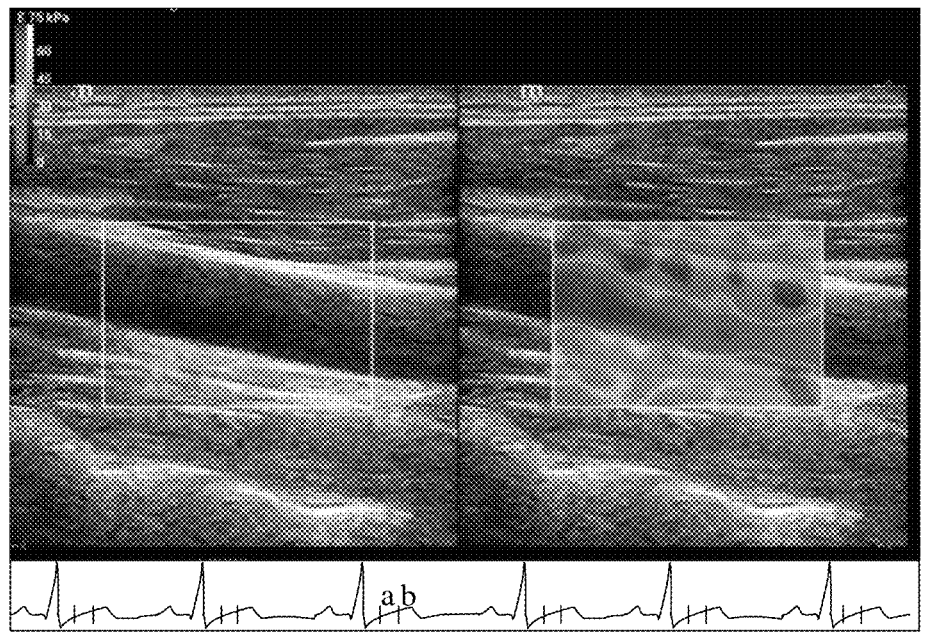
FIG. 10 is an exemplary schematic diagram in which a start time and an end time are marked in one embodiment of the present disclosure.

FIG. 10 is an exemplary schematic diagram showing the marking of the start time and the end time in one embodiment of the present disclosure. As shown in FIG. 10, the tissue in the left box is the target tissue, and the image in the right box is the elasticity image of the target tissue. The parts with different elasticity in the elasticity image may be represented by different colors. Under the image, the interference characteristic information, that is, the amplitude values of the ECG signal, are displayed in the form of ECG waveform, and the start time and the end time of the elasticity imaging process for obtaining such elasticity image is marked on the ECG waveform. Namely, the obtaining of such elasticity image is started at time a, and ended at time b.

In one embodiment of the present disclosure, an elasticity imaging method is provided, which may include: transmitting the ultrasound waves to the target tissue; receiving the ultrasound echoes of the ultrasound waves returned from the target tissue; obtaining the interference characteristic information that represents the degree of interference to the target tissue; and when the interference characteristic information does not meet the preset condition, stopping obtaining the elasticity image of the target tissue according to the ultrasound echoes. In the technical solution provided by the embodiment of the present disclosure, whether to obtain the elasticity image of the target tissue may be determined according to the interference characteristic information that represents the degree of interference to the target tissue, that is, the elasticity image may be obtained when the target tissue is weakly interfered. Therefore, the accuracy of the elasticity image is improved.

Figure 11:
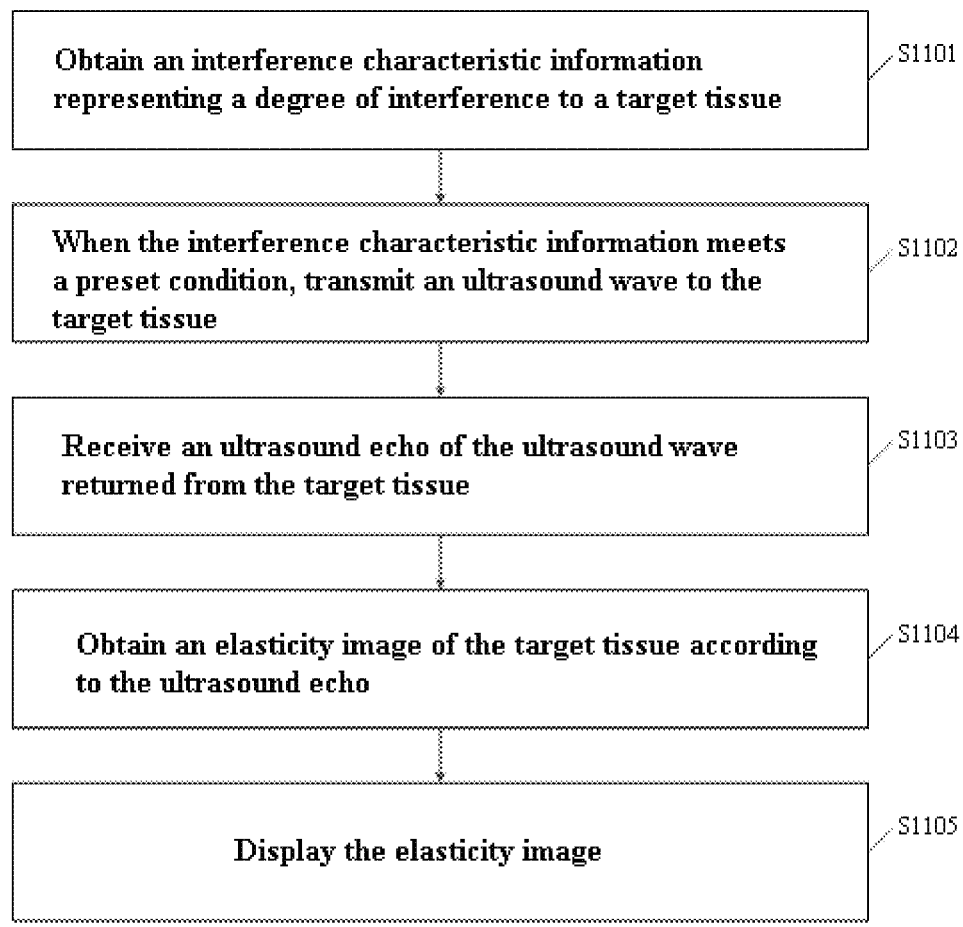
FIG. 11 is a schematic flow chart of an elasticity imaging method in one embodiment of the present disclosure.

FIG. 11 is a schematic flowchart of an elasticity imaging method in one embodiment of the present disclosure. As shown in FIG. 11, the method may include the following steps.

In step S1101, the interference characteristic information may be obtained. The interference characteristic information represents the degree of interference to the target tissue.

The obtaining of the interference characteristic information has been described in step S203, which will not be repeated here.

In step S1102, when the interference characteristic information meets the preset condition, the ultrasound waves may be transmitted to the target tissue.

In one embodiment of the present disclosure, after obtaining the interference characteristic information, the processor 101 of the elasticity imaging device may determine whether the interference characteristic information meets the preset condition, and when the interference characteristic information meets the preset condition, may control the ultrasound probe 105 to transmit the ultrasound waves to the target tissue.

In one embodiment of the present disclosure, after step S1101, the processor 101 of the elasticity imaging device may also determine whether the interference characteristic information meets the preset condition.

Specifically, in one embodiment of the present disclosure, the interference characteristic information may be the amplitude value of the ECG signal, and determining whether the interference characteristic information meet the preset condition after the processor 101 of the elasticity imaging device obtains the interference characteristic information may include the following ways.

It may be determined whether the amplitude value of the ECG signal is not greater than a first preset threshold. When it is not greater than the first preset threshold, the ultrasound waves may be transmitted to the target tissue.

Alternatively, it may be determined whether the amplitude value of the ECG signal is not greater than the first preset threshold and not less than a second preset threshold. When it is not greater than the first preset threshold and not less than the second preset threshold, the ultrasound waves may be transmitted to the target tissue.

Alternatively, the maximum amplitude value of the ECG signal may be obtained from the amplitude values of the ECG signal, and it may be determined whether the maximum amplitude value of the ECG signal is not greater than a third preset threshold. When the maximum amplitude value of the ECG signal is not greater than the third preset threshold, the ultrasound waves may be transmitted to the target tissue.

Alternatively, the maximum difference value of the amplitude values of the ECG signal may be determined according to the amplitude values of the ECG signal. It may be determined whether the maximum difference value of the amplitude values of the ECG signal is not greater than a fourth preset threshold. When the maximum difference value of the amplitude values of the ECG signal is not greater than the fourth preset threshold, the ultrasound waves may be transmitted to the target tissue.

Alternatively, the maximum amplitude value of the ECG signal may be determined from the amplitude values of the ECG signal, and a first time corresponding to the maximum amplitude value of the ECG signal may be determined. The ultrasound waves may be transmitted to the target tissue at a second time that is at a preset time interval from the first time.

In one embodiment of the present disclosure, the memory 102 of the elasticity imaging device may store the preset time interval, the first preset threshold, the second preset threshold, the third preset threshold and the fourth preset threshold. The preset time interval, the first preset threshold, the second preset threshold, the third preset threshold and the fourth preset threshold may be set by the user based on experience or actual needs, which will not be limited herein.

In one embodiment, the interference characteristic information is the amplitude value of the ECG signal. The amplitude value of the ECG signal obtained by the processor 101 of the elasticity imaging device is X1, and the first preset threshold is Y1. When X1 is not greater than Y1, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the ECG signal. The amplitude value of the ECG signal obtained by the processor 101 of the elasticity imaging device is X2, the first preset threshold is Y1, and the second preset threshold is Y2. When X2 is not greater than Y1 and not less than Y2, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the ECG signal. The processor 101 of the elasticity imaging device may obtain the amplitude values of the ECG signal within a period of time, and determine therefrom that the maximum amplitude value of the ECG signal is X3. The third preset threshold is Y3. When X3 is not greater than Y3, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the ECG signal. The processor 101 of the elasticity imaging device may obtain the amplitude values of the ECG signal within a period of time, and determines that the maximum difference value of the amplitude values of the ECG signal is X4. The fourth preset threshold is Y4. When X4 is not greater than Y4, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the ECG signal. The processor 101 of the elasticity imaging device may obtain the amplitude values of the ECG signal within a period of time, select the maximum amplitude value of the ECG signal therefrom, and further determine the first time corresponding to maximum amplitude value of the ECG signal as t1. The preset time interval is t. At the second time t2 that is at a time interval of t from t1, the interference characteristic information meets the preset conditions. In this case, the processor 101 of the elasticity imaging device may control the ultrasound probe 105 to transmit the ultrasound waves to the target tissue.

Specifically, in one embodiments of the present disclosure, the interference characteristic information may be the amplitude value of the respiratory wave signal, and determining whether the interference characteristic information meet the preset condition after the processor 101 of the elasticity imaging device obtains the interference characteristic information may include the following ways.

It may be determined whether the amplitude value of the respiratory wave signal is not greater than a first preset threshold. When it is not greater than the first preset threshold, the ultrasound waves may be transmitted to the target tissue.

Alternatively, it may be determined whether the amplitude value of the respiratory wave signal is not greater than the first preset threshold and not less than a second preset threshold. When it is not greater than the first preset threshold and not less than the second preset threshold, the ultrasound waves may be transmitted to the target tissue.

Alternatively, the maximum amplitude value of the respiratory wave signal may be obtained from the amplitude values of the respiratory wave signal, and it may be determined whether the maximum amplitude value of the respiratory wave signal is not greater than a third preset threshold. When the maximum amplitude value of the respiratory wave signal is not greater than the third preset threshold, the ultrasound waves may be transmitted to the target tissue.

Alternatively, the maximum difference value of the amplitude values of the respiratory wave signal may be determined according to the amplitude values of the respiratory wave signal. It may be determined whether the maximum difference value of the amplitude values of the respiratory wave signal is not greater than a fourth preset threshold. When the maximum difference value of the amplitude values of the respiratory wave signal is not greater than the fourth preset threshold, the ultrasound waves may be transmitted to the target tissue.

Alternatively, the maximum amplitude value of the respiratory wave signal may be determined from the amplitude values of the respiratory wave signal, and a first time corresponding to the maximum amplitude value of the respiratory wave signal may be determined. The ultrasound waves may be transmitted to the target tissue at a second time that is at a preset time interval from the first time.

In one embodiment, the interference characteristic information is the amplitude value of the respiratory wave signal. The amplitude value of the respiratory wave signal obtained by the processor 101 of the elasticity imaging device is M1, and the first preset threshold is Y1. When M1 is not greater than Y1, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the respiratory wave signal. The amplitude value of the respiratory wave signal obtained by the processor 101 of the elasticity imaging device is M2, the first preset threshold is Y1, and the second preset threshold is Y2. When M2 is not greater than Y1 and not less than Y2, the interference characteristic information meets the preset condition. In this case, the processor 101 of the elasticity imaging device may control the ultrasound probe 105 to transmit the ultrasound to the target tissue.

In one embodiment, the interference characteristic information is the amplitude value of the respiratory wave signal. The processor 101 of the elasticity imaging device may obtain the amplitude values of the respiratory wave signal within a period of time, and determine therefrom that the maximum amplitude value of the respiratory wave signal is M3. The third preset threshold is Y3. When M3 is not greater than Y3, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the respiratory wave signal. The processor 101 of the elasticity imaging device may obtain the amplitude values of the respiratory wave signal within a period of time, and determines that the maximum difference value of the amplitude values of the respiratory wave signal is M4. The fourth preset threshold is Y4. When M4 is not greater than Y4, the interference characteristic information meets the preset condition. In this case, the processor 101 of the elasticity imaging device may control the ultrasound probe 105 to transmit the ultrasound waves to the target tissue.

In one embodiment, the interference characteristic information is the amplitude value of the respiratory wave signal. The processor 101 of the elasticity imaging device may obtain the amplitude values of the respiratory wave signal within a period of time, select the maximum amplitude value of the respiratory wave signal therefrom, and further determine the first time corresponding to maximum amplitude value of the respiratory wave signal as t1. The preset time interval is t. At the second time t2 that is at an interval of t from t1, the interference characteristic information meets the preset conditions. In this case, the processor 101 of the elasticity imaging device may control the ultrasound probe 105 to transmit the ultrasound waves to the target tissue.

Specifically, in one embodiments of the present disclosure, the interference characteristic information may be the displacement value of the target tissue, and determining whether the interference characteristic information meet the preset condition after the processor 101 of the elasticity imaging device obtains the interference characteristic information may include the following ways.

It may be determined whether the displacement value of the target tissue is not greater than a first preset threshold.

When it is not greater than the first preset threshold, the ultrasound waves may be transmitted to the target tissue.

Alternatively, it may be determined whether the displacement value of the target tissue is not greater than the first preset threshold and not less than a second preset threshold. When it is not greater than the first preset threshold and not less than the second preset threshold, the ultrasound waves may be transmitted to the target tissue.

Alternatively, the maximum displacement value of the target tissue may be obtained from the displacement values of the target tissue, and it may be determined whether the maximum displacement value of the target tissue is not greater than a third preset threshold. When the maximum displacement value of the target tissue is not greater than the third preset threshold, the ultrasound waves may be transmitted to the target tissue.

Alternatively, the maximum difference value of the displacement values of the target tissue may be determined according to the displacement values of the target tissue. It may be determined whether the maximum difference value of the displacement values of the target tissue is not greater than a fourth preset threshold. When the maximum difference value of the displacement values of the target tissue is not greater than the fourth preset threshold, the ultrasound waves may be transmitted to the target tissue.

Alternatively, the maximum displacement value of the target tissue may be determined from the displacement values of the target tissue, and a first time corresponding to the maximum displacement value of the target tissue may be determined. The ultrasound waves may be transmitted to the target tissue at a second time that is at a preset time interval from the first time.

In one embodiment, the interference characteristic information is the displacement value of the target tissue. The displacement value of the target tissue obtained by the processor 101 of the elasticity imaging device is P1, and the first preset threshold is Y1. When P1 is not greater than Y1, the interference characteristic information meets the preset condition. In this case, the processor 101 of the elasticity imaging device may control the ultrasound probe 105 to transmit the ultrasound waves to the target tissue.

In one embodiment, the interference characteristic information is the displacement value of the target tissue. The displacement value of the target tissue obtained by the processor 101 of the elasticity imaging device is P2, the first preset threshold is Y1, and the second preset threshold is Y2. When P2 is not greater than Y1 and not less than Y2, the interference characteristic information meets the preset condition. In this case, the processor 101 of the elasticity imaging device may control the ultrasound probe 105 to transmit the ultrasound waves to the target tissue.

In one embodiment, the interference characteristic information is the displacement value of the target tissue. The processor 101 of the elasticity imaging device may obtain the displacement values of the target tissue within a period of time, and determine therefrom that the maximum displacement value of the target tissue is P3. The third preset threshold is Y3. When P3 is not greater than Y3, the interference characteristic information meets the preset condition. In this case, the processor 101 of the elasticity imaging device may control the ultrasound probe 105 to transmit the ultrasound waves to the target tissue.

In one embodiment, the interference characteristic information is the displacement value of the target tissue. The processor 101 of the elasticity imaging device may obtain the displacement values of the target tissue within a period of time, and determines that the maximum difference value of the displacement values of the target tissue is P4. The fourth preset threshold is Y4. When P4 is not greater than Y4, the interference characteristic information meets the preset condition. In this case, the processor 101 of the elasticity imaging device may control the ultrasound probe 105 to transmit the ultrasound waves to the target tissue.

In one embodiment, the interference characteristic information is the displacement value of the target tissue. The processor 101 of the elasticity imaging device may obtain the displacement values of the target tissue within a period of time, select the maximum displacement value of the target tissue therefrom, and further determine the first time corresponding to maximum displacement value of the target tissue as t1. The preset time interval is t. At the second time t2 that is at a time interval of t from t1, the interference characteristic information meets the preset conditions. In this case, the processor 101 of the elasticity imaging device may control the ultrasound probe 105 to transmit the ultrasound waves to the target tissue.

In one embodiment of the present disclosure, the processor 101 of the elasticity imaging device may first determine whether the interference characteristic information meets the preset condition. When the interference characteristic information meets the preset condition, it means that the target tissue is currently in a relatively stable state, which is beneficial to obtain the elasticity image of the target tissue, and therefore the ultrasound probe 105 may be controlled to transmit the ultrasound waves to the target tissue, that is, the elasticity imaging may be triggered.

In one embodiment of the present disclosure, when the interference characteristic information does not meet the preset condition, it means that the target tissue is currently in a non-stationary state, which is not beneficial to obtain the elasticity image of the target tissue, and therefore the processor 101 of the elasticity imaging device may stop the transmitting of the ultrasound waves to the target tissue.

In step S1103, the ultrasound echoes of the ultrasound waves returned from the target tissue may be received.

The step S1103 may be consistent with the step S202, and will not be repeated here.

In step S1104, the elasticity image of the target tissue may be obtained according to the ultrasound echoes.

The step S1104 may be consistent with the step S205, and will not be repeated here.

In step S1105, the elasticity image may be displayed.

In one embodiment of the present disclosure, after the processor 101 of the elasticity imaging device obtains the elasticity image of the target tissue, the display 104 may display the elasticity image.

It is understandable that, in one embodiment of the present disclosure, since the processor 101 of the elasticity imaging device obtains the elasticity image of the target tissue when the interference characteristic information meets the preset condition, that is, when the target tissue is in a stable state, the elasticity image can more accurately represent the elasticity of the target tissue. The display 104 may directly display the elasticity image.

In one embodiment of the present disclosure, after step S1101, there may further be a step S1106.

In step S1106, the interference characteristic information may be displayed.

The step S1106 may be similar to step S206, and will not be repeated here.

In one embodiment of the present disclosure, after step S1106, there may further be a step S1107 or S1108.

In step S1107, a third control instruction may be received. The third control instruction may instruct to stop transmitting the ultrasound waves to the target tissue.

In one embodiment of the present disclosure, after the display 104 of the elasticity imaging device displays the interference characteristic information, the processor 101 may receive the third control instruction that instruct to stop transmitting the ultrasound waves to the target tissue.

It is understandable that, in one embodiment of the present disclosure, the memory 102 of the elasticity imaging device may also pre-store a corresponding standard value for the user to view so as to compare it with the displayed interference characteristic information to determine whether to send the corresponding control instructions to the elasticity imaging device.

In step S1108, a fourth control instruction may be received. The fourth control instruction may instruct to transmit the ultrasound waves to the target tissue.

In one embodiment of the present disclosure, after the display 104 of the elasticity imaging device display the interference characteristic information, the fourth control instruction instructing to transmit the ultrasound waves to the target tissue may be received.

In one embodiment of the present disclosure, the third control instruction and the fourth control instruction may be inputted to the processor 101 of the elasticity imaging device by the user through a button or a touch interface on the elasticity imaging device based on the interference characteristic information displayed on the display 104 of the elasticity imaging device.

It is understandable that, in one embodiment of the present disclosure, the user may autonomously determine whether it is currently suitable to control the ultrasound probe to transmit the ultrasound waves to the target tissue to obtain the elasticity image of the target tissue based on the interference characteristic information displayed on the display 104 of the elasticity imaging device. For example, when the interference characteristic information is the amplitude value of the ECG signal, when the user sees that the amplitude value of the ECG signal fluctuates sharply, it can be determined that the target tissue is currently in a non-stationary state. At this time, if the ultrasound probe is controlled to transmit the ultrasound wave to the target tissue and the elasticity image is obtained according to the ultrasound echoes, the obtained elasticity image will be inaccurate. Therefore, the user can input the third control instruction to the elasticity imaging device. When the user sees that the amplitude value of the ECG signal fluctuates relatively smoothly, it can be determined that the target tissue is currently in a stable state. At this time, if the ultrasound probe is controlled to transmit the ultrasound wave to the target tissue and the elasticity image is obtained according to the ultrasound echoes, the obtained elasticity image will be accurate. Therefore, the user can input the fourth control instruction to the elasticity imaging device.

In one embodiment of the present disclosure, the processor 101 of the elasticity imaging device may also determine the start time and the end time corresponding to the elasticity image, and mark the start time and the end time.

In one embodiment of the present disclosure, the processor 101 of the elasticity imaging device may mark the start time and the end time corresponding to the elasticity image in different ways. For example, the start time and the end time may be marked on the interference characteristic information displayed on the display 104, or be marked on the interface of the displayed elasticity image. In addition, different colors or different shapes (such as vertical lines, small triangles, etc.) may also be used to mark the start time and the end time. The ways for marking the start time and the end time will not be limited herein.

In one embodiment of the present disclosure, an elasticity imaging method may be provided, which may include: obtaining the interference characteristic information that represents the degree of interference to the target tissue; when the interference characteristic information meets the preset condition, transmitting the ultrasound waves to the target tissue; receiving the ultrasound echoes of the ultrasound waves returned from the target tissue; obtaining the elasticity image of the target tissue according to the ultrasound echoes; and displaying the elasticity image. In the technical solution provided by this embodiment, whether to transmit the ultrasound waves may be determined according to the interference characteristic information representing the degree of interference to the target tissue, so as to obtain the elasticity image of the target tissue. For the strain-type elasticity imaging method, it can ensure that the elasticity image is obtained in a uniform pressure of the probe. For the shear-wave elasticity imaging method, the shear wave signal can be accurately captured. Therefore, the accuracy of the elasticity image is improved.

Figure 12:
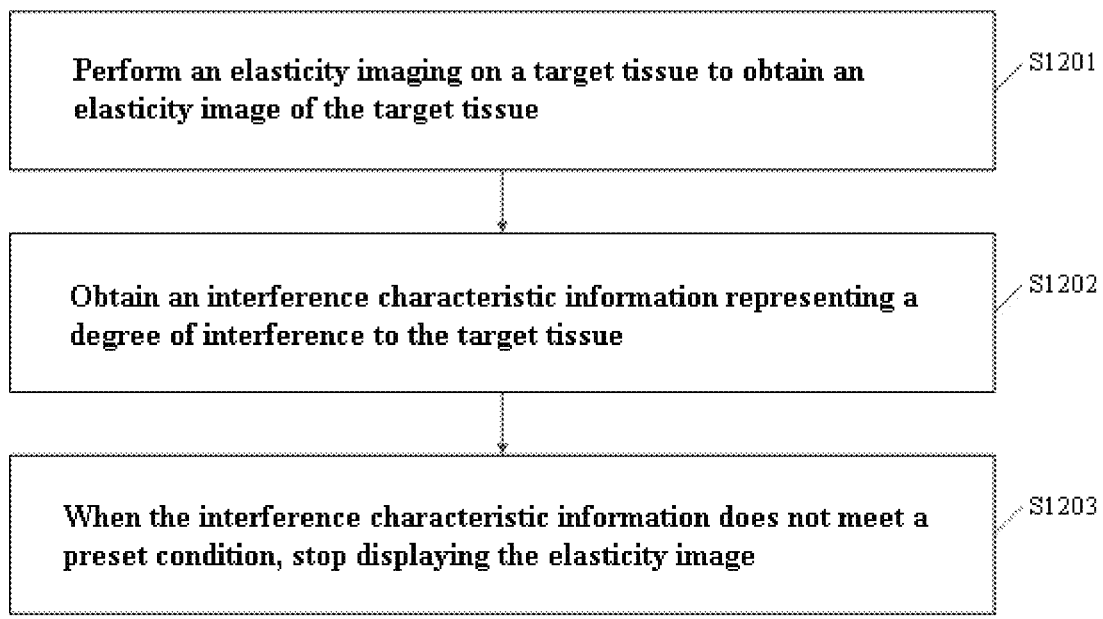
FIG. 12 is a schematic flow chart of an elasticity imaging method in one embodiment of the present disclosure.

FIG. 12 is a schematic flow chart of an elasticity imaging method in one embodiment of the present disclosure. As shown in FIG. 12, the method may include the following steps.

In step S1201, an elasticity imaging may be performed on the target tissue to obtain an elasticity image of the target tissue.

In one embodiment of the present disclosure, the processor 101 of the elasticity imaging device may perform the elasticity imaging on the target tissue to obtain the elasticity image of the target tissue.

Specifically, in one embodiment of the present disclosure, the processor 101 of the elasticity imaging device performing the elasticity imaging on the target tissue to obtain the elasticity image of the target tissue may include: controlling the ultrasound probe 105 to transmit the ultrasound waves to the target tissue; receiving the ultrasound echoes of the ultrasound waves returned from the target tissue through the ultrasound probe; determining the deformation parameter of the target tissue according to the ultrasound echoes; and obtaining the elasticity image of the target tissue according to the deformation parameter.

Specifically, in one embodiment of the present disclosure, the processor 101 of the elasticity imaging device performing the elasticity imaging on the target tissue to obtain the elasticity image of the target tissue may include: controlling the ultrasound probe 105 to propagate a shear wave to the target tissue; controlling the ultrasound probe to transmit the ultrasound waves to the target tissue; receiving the ultrasound echoes of the ultrasound waves returned from the target tissue through the ultrasound probe; determining the propagation parameter of the shear wave according to the ultrasound echo; and obtaining the elasticity image of the target tissue according to the propagation parameter.

Specifically, in one embodiment of the present disclosure, the processor 101 of the elasticity imaging device may further control the ultrasound probe 105 to transmit the ultrasound waves to the target tissue, receive the ultrasound echoes of the ultrasound waves returned from the target tissue, determine the tissue parameter information of the target tissue according to the ultrasound echoes, and display the tissue parameter information.

Obtaining the elasticity image of the target tissue and displaying the tissue parameter information have been described above, and will not be repeated here.

In step S1202, the interference characteristic information may be obtained, where the interference characteristic information represents the degree of interference to the target tissue.

Obtaining the interference characteristic information has been described in step S203, and will not be repeated here.

In step S1203, when the interference characteristic information does not meet a preset condition, displaying the elasticity image may be stopped.

In one embodiment of the present disclosure, after obtaining the interference characteristic information, the processor 101 of the elasticity imaging device may determine whether the interference characteristic information meets the preset condition. When the interference characteristic information does not meet the preset condition, the display 104 may stop displaying the elasticity image.

In one embodiment of the present disclosure, after step S1202, the processor 101 of the elasticity imaging device may determine whether the interference characteristic information meets the preset condition.

Specifically, in one embodiment of the present disclosure, the interference characteristic information may be the amplitude value of the ECG signal, and determining whether the interference characteristic information meet the preset condition after the processor 101 of the elasticity imaging device obtains the interference characteristic information may include the following ways.

It may be determined whether the amplitude value of the ECG signal is not greater than a first preset threshold. When it is greater than the first preset threshold, displaying of the elasticity image may be stopped.

Alternatively, it may be determined whether the amplitude value of the ECG signal is not greater than the first preset threshold and not less than a second preset threshold. When it is greater than the first preset threshold or less than the second preset threshold, displaying of the elasticity image may be stopped.

Alternatively, the maximum amplitude value of the ECG signal may be obtained from the amplitude values of the ECG signal, and it may be determined whether the maximum amplitude value of the ECG signal is not greater than a third preset threshold. When the maximum amplitude value of the ECG signal is greater than the third preset threshold, displaying of the elasticity image may be stopped.

Alternatively, the maximum difference value of the amplitude values of the ECG signal may be determined according to the amplitude values of the ECG signal. It may be determined whether the maximum difference value of the amplitude values of the ECG signal is not greater than a fourth preset threshold. When the maximum difference value of the amplitude values of the ECG signal is greater than the fourth preset threshold, displaying of the elasticity image may be stopped.

Alternatively, the maximum amplitude value of the ECG signal may be determined from the amplitude values of the ECG signal, and a first time corresponding to the maximum amplitude value of the ECG signal may be determined. Displaying of the elasticity image may be stopped may be stopped at a second time that is at a preset time interval from the first time.

In one embodiment of the present disclosure, the memory 102 of the elasticity imaging device may store the preset time interval, the first preset threshold, the second preset threshold, the third preset threshold and the fourth preset threshold. The preset time interval, the first preset threshold, the second preset threshold, the third preset threshold and the fourth preset threshold may be set by the user based on experience or actual needs, which will not be limited herein.

In one embodiment, the interference characteristic information is the amplitude value of the ECG signal. The amplitude value of the ECG signal obtained by the processor 101 of the elasticity imaging device is $X1$, and the first preset threshold is $Y1$. When $X1$ is greater than $Y1$, the interference characteristic information does not meet the preset condition. In this case, the display 104 may be controlled to stop displaying the elasticity image.

In one embodiment, the interference characteristic information is the amplitude value of the ECG signal. The amplitude value of the ECG signal obtained by the processor 101 of the elasticity imaging device is $X2$, the first preset threshold is $Y1$, and the second preset threshold is $Y2$. When $X2$ is greater than $Y1$ or $X2$ is less than $Y2$, the interference characteristic information does not meet the preset condition. In this case, the display 104 may be controlled to stop displaying the elasticity image.

In one embodiment, the interference characteristic information is the amplitude value of the ECG signal. The processor 101 of the elasticity imaging device may obtain the amplitude values of the ECG signal within a period of time, and determine therefrom that the maximum amplitude value of the ECG signal is $X3$. The third preset threshold is $Y3$. When $X3$ is greater than $Y3$, the interference characteristic information does not meet the preset condition. In this case, the display 104 may be controlled to stop displaying the elasticity image.

In one embodiment, the interference characteristic information is the amplitude value of the ECG signal. The processor 101 of the elasticity imaging device may obtain the amplitude values of the ECG signal within a period of time, and determines that the maximum difference value of the amplitude values of the ECG signal is $X4$. The fourth preset threshold is $Y4$. When $X4$ is greater than $Y4$, the interference characteristic information does not meet the preset condition. In this case, the display 104 may be controlled to stop displaying the elasticity image.

In one embodiment, the interference characteristic information is the amplitude value of the ECG signal. The processor 101 of the elasticity imaging device may obtain the amplitude values of the ECG signal within a period of time, select the maximum amplitude value of the ECG signal therefrom, and further determine the first time corresponding to maximum amplitude value of the ECG signal as $t1$. The preset time interval is $t$. At a second time $t2$ that is at an interval of $t$ from $t1$, the interference characteristic information does not meet the preset conditions. In this case, the display 104 may be controlled to stop displaying the elasticity image.

Specifically, in one embodiments of the present disclosure, the interference characteristic information may be the amplitude value of the respiratory wave signal, and determining whether the interference characteristic information meet the preset condition after the processor 101 of the elasticity imaging device obtains the interference characteristic information may include the following ways.

It may be determined whether the amplitude value of the respiratory wave signal is not greater than a first preset threshold. When it is greater than the first preset threshold, displaying of the elasticity image may be stopped.

Alternatively, it may be determined whether the amplitude value of the respiratory wave signal is not greater than the first preset threshold and not less than a second preset threshold. When it is greater than the first preset threshold or less than the second preset threshold, displaying of the elasticity image may be stopped.

Alternatively, the maximum amplitude value of the respiratory wave signal may be obtained from the amplitude values of the respiratory wave signal, and it may be determined whether the maximum amplitude value of the respiratory wave signal is not greater than a third preset threshold. When the maximum amplitude value of the respiratory wave signal is greater than the third preset threshold, displaying of the elasticity image may be stopped.

Alternatively, the maximum difference value of the amplitude values of the respiratory wave signal may be determined according to the amplitude values of the respiratory wave signal. It may be determined whether the maximum difference value of the amplitude values of the respiratory wave signal is not greater than a fourth preset threshold. When the maximum difference value of the amplitude values of the respiratory wave signal is greater than the fourth preset threshold, displaying of the elasticity image may be stopped.

Alternatively, the maximum amplitude value of the respiratory wave signal may be determined from the amplitude values of the respiratory wave signal, and a first time corresponding to the maximum amplitude value of the respiratory wave signal may be determined. Displaying of the elasticity image may be stopped at a second time that is at a preset time interval from the first time.

In one embodiment, the interference characteristic information is the amplitude value of the respiratory wave signal. The amplitude value of the respiratory wave signal obtained by the processor 101 of the elasticity imaging device is M1, and the first preset threshold is Y1. When M1 is greater than Y1, the interference characteristic information does not meet the preset condition. In this case, the display 104 may be controlled to stop displaying the elasticity image.

In one embodiment, the interference characteristic information is the amplitude value of the respiratory wave signal. The amplitude value of the respiratory wave signal obtained by the processor 101 of the elasticity imaging device is M2, the first preset threshold is Y1, and the second preset threshold is Y2. When M2 is greater than Y1 or M2 is less than Y2, the interference characteristic information does not meet the preset condition. In this case, the display 104 may be controlled to stop displaying the elasticity image.

In one embodiment, the interference characteristic information is the amplitude value of the respiratory wave signal. The processor 101 of the elasticity imaging device may obtain the amplitude values of the respiratory wave signal within a period of time, and determine therefrom that the maximum amplitude value of the respiratory wave signal is M3. The third preset threshold is Y3. When M3 is greater than Y3, the interference characteristic information does not meet the preset condition. In this case, the display 104 may be controlled to stop displaying the elasticity image.

In one embodiment, the interference characteristic information is the amplitude value of the respiratory wave signal. The processor 101 of the elasticity imaging device may obtain the amplitude values of the respiratory wave signal within a period of time, and determines that the maximum difference value of the amplitude values of the respiratory wave signal is M4. The fourth preset threshold is Y4. When M4 is greater than Y4, the interference characteristic information does not meet the preset condition. In this case, the display 104 may be controlled to stop displaying the elasticity image.

In one embodiment, the interference characteristic information is the amplitude value of the respiratory wave signal. The processor 101 of the elasticity imaging device may obtain the amplitude values of the respiratory wave signal within a period of time, select the maximum amplitude value of the respiratory wave signal therefrom, and further determine the first time corresponding to maximum amplitude value of the respiratory wave signal as t1. The preset time interval is t. At the second time t2 that is at an interval of t from t1, the interference characteristic information does not meet the preset conditions. In this case, the display 104 may be controlled to stop displaying the elasticity image.

Specifically, in one embodiments of the present disclosure, the interference characteristic information may be the displacement value of the target tissue, and determining whether the interference characteristic information meet the preset condition after the processor 101 of the elasticity imaging device obtains the interference characteristic information may include the following ways.

It may be determined whether the displacement value of the target tissue is not greater than a first preset threshold. When it is greater than the first preset threshold, displaying of the elasticity image may be stopped.

Alternatively, it may be determined whether the displacement value of the target tissue is not greater than a first preset threshold and not less than a second preset threshold. When it is greater than the first preset threshold or less than the second preset threshold, displaying of the elasticity image may be stopped.

Alternatively, the maximum displacement value of the target tissue may be obtained from the displacement values of the target tissue, and it may be determined whether the maximum displacement value of the target tissue is not greater than a third preset threshold. When the maximum displacement value of the target tissue is greater than the third preset threshold, displaying of the elasticity image may be stopped.

Alternatively, the maximum difference value of the displacement values may be determined according to the displacement values of the target tissue. It may be determined whether the maximum difference value of the displacement values is not greater than a fourth preset threshold. When the maximum difference value of the displacement values is greater than the fourth preset threshold, displaying of the elasticity image may be stopped.

Alternatively, the maximum displacement value may be determined from the displacement values of the target tissue, and a first time corresponding to the maximum displacement value may be determined. Displaying of the elasticity image may be stopped at a second time that is at a preset time interval from the first time.

In one embodiment, the interference characteristic information is the displacement value of the target tissue. The displacement value of the target tissue obtained by the processor 101 of the elasticity imaging device is P1, and the first preset threshold is Y1. When P1 is greater than Y1, the interference characteristic information does not meet the preset condition. In this case, the display 104 may be controlled to stop displaying the elasticity image.

In one embodiment, the interference characteristic information is the displacement value of the target tissue. The displacement value of the target tissue obtained by the processor 101 of the elasticity imaging device is P2, the first preset threshold is Y1, and the second preset threshold is Y2. When P2 is greater than Y1 or P2 is less than Y2, the interference characteristic information does not meet the preset condition. In this case, the display 104 may be controlled to stop displaying the elasticity image.

In one embodiment, the interference characteristic information is the displacement value of the target tissue. The processor 101 of the elasticity imaging device may obtain multiple displacement values of the target tissue within a period of time, and determine therefrom that the maximum displacement value is P3. The third preset threshold is Y3. When P3 is greater than Y3, the interference characteristic information does not meet the preset condition. In this case, the display 104 may be controlled to stop displaying the elasticity image.

In one embodiment, the interference characteristic information is the displacement value of the target tissue. The processor 101 of the elasticity imaging device may obtain multiple displacement values of the target tissue within a period of time, and determines that the maximum difference value of the displacement values is P4. The fourth preset threshold is Y4. When P4 is greater than Y4, the interference characteristic information does not meet the preset condition. In this case, the display 104 may be controlled to stop displaying the elasticity image.

In one embodiment, the interference characteristic information is the displacement value of the target tissue. The processor 101 of the elasticity imaging device may obtain multiple displacement values of the target tissue within a period of time, select the maximum displacement value therefrom, and further determine the first time corresponding to maximum displacement value as t1. The preset time interval is t. At a second time t2 that is at an interval of t from t1, the interference characteristic information does not meet the preset conditions. In this case, the display 104 may be controlled to stop displaying the elasticity image.

In one embodiment of the present disclosure, when the processor 101 of the elasticity imaging device determines that the interference characteristic information meets the preset condition, the display 104 may display the elasticity image.

In one embodiment of the present disclosure, after step S1202, there may further be step S1204.

In step S1204, the interference characteristic information may be displayed.

The step S1024 may be similar to step S206, and will not be repeated here.

In one embodiment of the present disclosure, after step S1204, there may further be step S1205 or S1206.

In step S1205, a fifth control instruction may be received, where the fifth control instruction instruct to stop displaying the elasticity image.

In one embodiment of the present disclosure, after the display 104 of the elasticity imaging device displays the interference characteristic information, the processor 101 may receive the fifth control instruction that instructs to stop displaying the elasticity image.

It is understandable that, in one embodiment of the present disclosure, the memory 102 of the elasticity imaging device may also pre-store a corresponding standard value for the user to view so as to compare it with the displayed interference characteristic information to determine whether to send the corresponding control instructions to the elasticity imaging device.

In step S1206, a sixth control instruction may be received. The sixth control instruction may instruct to display the elasticity image.

In one embodiment of the present disclosure, after the display 104 of the elasticity imaging device displays the interference characteristic information, the sixth control instruction that instructs to display the elasticity image may be received.

In one embodiment of the present disclosure, the fifth control instruction and the sixth control instruction may be inputted to the processor 101 of the elasticity imaging device by the user through a button or a touch interface on the elasticity imaging device based on the interference characteristic information displayed on the display 104 of the elasticity imaging device.

It is understandable that, in one embodiment of the present disclosure, the user can autonomously determine whether to display the elasticity image currently according to the interference characteristic information displayed on the display 104 of the elasticity imaging device. For example, the interference characteristic information is the amplitude value of the ECG signal. When the user sees that the amplitude value of the ECG signal fluctuates sharply, the fifth control instruction may be sent to the elasticity imaging device. When the user sees the amplitude value of the ECG signal fluctuates relatively smoothly, the sixth control instruction may be sent to the elasticity imaging device.

In one embodiment of the present disclosure, the processor 101 of the elasticity imaging device may also determine the start time and the end time corresponding to the elasticity image, and mark the start time and the end time.

In one embodiment of the present disclosure, the processor 101 of the elasticity imaging device may mark the start time and the end time corresponding to the elasticity image in different ways. For example, the start time and the end time may be marked on the interference characteristic information displayed on the display 104, or be marked on the interface of the displayed elasticity image. In addition, different colors or different shapes (such as vertical lines, small triangles, etc.) may also be used to mark the start time and the end time. The ways for marking the start time and the end time will not be limited herein.

In one embodiment of the present disclosure, an elasticity imaging method is provided, which may include: performing the elasticity imaging on a target tissue to obtain the elasticity image of the target tissue; obtaining the interference characteristic information that represents the degree of interference to the target tissue; and when the interference characteristic information does not meet the preset conditions, stopping displaying the elasticity image. In the technical solution provided in this embodiment, whether to display the elasticity image of the target tissue may be determined according to the interference characteristic information that represents the degree of interference to the target tissue, thereby improving the intelligence of the elasticity image display.

Those skilled in the art will understand that the embodiments of the present disclosure may be provided as a method, a system or a computer program product. Therefore, the present disclosure may be implemented in hardware, software or combination thereof. Moreover, the present disclosure may be implemented in the form of a computer program product implemented on one or more computer-readable storage media (including but not limited to disk storage, optical storage, etc.) containing computer-usable program codes.

The present disclosure has been described with reference to the flow charts and/or block diagrams of the methods, devices (systems) and computer program products in the embodiments of the present disclosure. It should be understood that each process and/or block in the flow chart and/or block diagram, and the combination of the processes and/or blocks in the flow charts and/or block diagrams, can be implemented by computer program instructions. These computer program instructions can be provided to the processor of a general-purpose computer, a special-purpose computer, an embedded processor or other programmable signal processing device to form a machine, such that the instructions executed by the processor of the computer or other programmable signal processing device generate a device that implements one or more processes in the flow chart and/or implements the function specified in one or more blocks in the block diagram.

The computer program instructions may also be stored in a computer-readable memory that can direct a computer or other programmable signal processing device to work in a specific manner, such that the instructions stored in the computer-readable memory produce an article of manufacture including the instruction device. The instruction device implements one or more processes in the flow chart and/or implements the function specified in one or more blocks in the block diagram.

The computer program instructions may also be loaded into a computer or other programmable signal processing device, such that a series of operation steps can be executed in the computer or other programmable device to produce computer-implemented processing. Thereby, the instructions executed in the computer or other programmable device can provide steps for implementing one or more processes in the flow chart and/or implements the function specified in one or more blocks in the block diagram.

The embodiments of the present disclosure have been described above, which will not intend to limit the protection scope of the present disclosure.

What is claimed is:

1. An elasticity imaging method, comprising:
transmitting an ultrasound wave to a target tissue;
receiving an ultrasound echo of the ultrasound wave returned from the target tissue;
obtaining an interference characteristic information, wherein the interference characteristic information represents a degree of interference to the target tissue;
displaying an interference characteristic waveform corresponding to the interference characteristic information;
determining whether the interference characteristic information meets a preset condition based on a degree of change in an amplitude value of the interference characteristic waveform;
when the interference characteristic information meets the preset condition, obtaining an elasticity image of the target tissue according to the ultrasound echo; and
when the interference characteristic information does not meet the preset condition, stopping obtaining the elasticity image of the target tissue according to the ultrasound echo,
wherein the interference characteristic information meeting the preset condition comprises: a maximum amplitude value or a maximum difference value of amplitude values of the interference characteristic waveform is not greater than a preset threshold, and the interference characteristic information not meeting the preset condition comprises: the maximum amplitude value or the maximum difference value of the amplitude values of the interference characteristic waveform is greater than the preset threshold.

2. The method of claim 1, after displaying the interference characteristic waveform, further comprising:
receiving a first control instruction, wherein the first control instruction instructs to stop obtaining the elasticity image of the target tissue according to the ultrasound echo.

3. The method of claim 1, after displaying the interference characteristic waveform, further comprising:
receiving a second control instruction, wherein the second control instruction instructs to obtain the elasticity image of the target tissue according to the ultrasound echo.

4. The method of claim 1, wherein obtaining the elasticity image of the target tissue according to the ultrasound echo comprises:
determining a deformation parameter of the target tissue according to the ultrasound echo; and
obtaining the elasticity image of the target tissue according to the deformation parameter.

5. The method of claim 1, wherein obtaining the elasticity image of the target tissue according to the ultrasound echo comprises:
determining a propagation parameter of a shear wave propagating in the target tissue according to the ultrasound echo; and
obtaining the elasticity image of the target tissue according to the propagation parameter.

6. The method of claim 1, further comprising:
determining a tissue parameter information of the target tissue according to the ultrasound echo; and
displaying the tissue parameter information.

7. The method of claim 1, wherein the interference characteristic information comprises at least one of an amplitude value of an ECG signal, an amplitude value of a respiratory wave signal and a displacement value of the target tissue.

8. The method of claim 7, wherein, the interference characteristic information is the amplitude value of the ECG signal, and after obtaining the interference characteristic information, the method further comprises:
determining whether the amplitude value of the ECG signal is not greater than a first preset threshold, and when the amplitude value of the ECG signal is greater than the first preset threshold, stopping obtaining the elasticity image of the target tissue according to the ultrasound echo; or
determining whether the amplitude value of the ECG signal is not greater than a first preset threshold and not less than a second preset threshold, and when the amplitude value of the ECG signal is greater than the first preset threshold or less than the second preset threshold, stopping obtaining the elasticity image of the target tissue according to the ultrasound echo; or
determining a maximum amplitude value of the ECG signal from amplitude values of the ECG signal, determining whether the maximum amplitude value of the ECG signal is not greater than a third preset threshold, and when the maximum amplitude value of the ECG signal is greater than the third preset threshold, stopping obtaining the elasticity image of the target tissue according to the ultrasound echo; or
determining a maximum difference value of the amplitude values of the ECG signal according to the amplitude values of the ECG signal, determining whether the maximum difference value is not greater than a fourth preset threshold, and when the maximum difference value is greater than the fourth preset threshold, stopping obtaining the elasticity image of the target tissue according to the ultrasound echo; or determining a maximum amplitude value of the ECG signal from the amplitude values of the ECG signal, determining a first time corresponding to the maximum amplitude value of the ECG signal, and stopping obtaining the elasticity image of the target tissue according to the ultrasound echo at a second time that is at a preset time interval from the first time.

9. The method of claim 7, wherein, the interference characteristic information is the amplitude value of the respiratory wave signal, and after obtaining the interference characteristic information, the method further comprises:
  determining whether the amplitude value of the respiratory wave signal is not greater than a first preset threshold, and when the amplitude value of the respiratory wave signal is greater than the first preset threshold, stopping obtaining the elasticity image of the target tissue according to the ultrasound echo; or
  determining whether the amplitude value of the respiratory wave signal is not greater than a first preset threshold and not less than a second preset threshold, and when the amplitude value of the respiratory wave signal is greater than the first preset threshold or less than the second preset threshold, stopping obtaining the elasticity image of the target tissue according to the ultrasound echo; or
  determining a maximum amplitude value of the respiratory wave signal from amplitude values of the respiratory wave signal, determining whether the maximum amplitude value of the respiratory wave signal is not greater than a third preset threshold, and when the maximum amplitude value of the respiratory wave signal is greater than the third preset threshold, stopping obtaining the elasticity image of the target tissue according to the ultrasound echo; or
  determining a maximum difference value of the amplitude values of the respiratory wave signal according to the amplitude values of the respiratory wave signal, determining whether the maximum difference value is not greater than a fourth preset threshold, and when the maximum difference value is greater than the fourth preset threshold, stopping obtaining the elasticity image of the target tissue according to the ultrasound echo; or
  determining a maximum amplitude value of the respiratory wave signal from the amplitude values of the respiratory wave signal, determining a first time corresponding to the maximum amplitude value of the respiratory wave signal, and stopping obtaining the elasticity image of the target tissue according to the ultrasound echo at a second time that is at a preset time interval from the first time.

10. The method of claim 7, wherein, the interference characteristic information is the displacement value of the target tissue, obtaining the interference characteristic information comprises:
  obtaining a first ultrasound data of the target tissue at a first time;
  obtaining a first position information of the target tissue according to the first ultrasound data;
  obtaining a second ultrasound data of the target tissue at a second time;
  obtaining a second position information of the target tissue according to the second ultrasound data; and
  determining the displacement value of the target tissue according to the first position information and the second position information; and after obtaining the interference characteristic information, the method further comprises:
  determining whether the displacement value of the target tissue is not greater than a first preset threshold, and when the displacement value of the target tissue is greater than the first preset threshold, stopping obtaining the elasticity image of the target tissue according to the ultrasound echo; or
  determining whether the displacement value of the target tissue is not greater than a first preset threshold and not less than a second preset threshold, and when displacement value of the target tissue is greater than the first preset threshold or less than the second preset threshold, stopping obtaining the elasticity image of the target tissue according to the ultrasound echo; or
  determining a maximum displacement value of the target tissue from the displacement values of the target tissue, determining whether the maximum displacement value of the target tissue is not greater than a third preset threshold, and when the maximum displacement value of the target tissue is greater than the third preset threshold, stopping obtaining the elasticity image of the target tissue according to the ultrasound echo; or
  determining a maximum difference value of the displacement values of the target tissue according to the displacement values of the target tissue, determining whether the maximum difference value is not greater than a fourth preset threshold, and when the maximum difference value is greater than the fourth preset threshold, stopping obtaining the elasticity image of the target tissue according to the ultrasound echo; or
  determining a maximum displacement value of the target tissue from the displacement values of the target tissue, determining a first time corresponding to the maximum displacement value of the target tissue, and stopping obtaining the elasticity image of the target tissue according to the ultrasound echo at a second time that is at a preset time interval from the first time.

11. An elasticity imaging method, comprising:
  obtaining an interference characteristic information, wherein the interference characteristic information represents a degree of interference to a target tissue;
  displaying an interference characteristic waveform corresponding to the interference characteristic information;
  determining whether the interference characteristic information meets a preset condition based on a degree of change in an amplitude value of the interference characteristic waveform; and
  when the interference characteristic information meets the preset condition, transmitting an ultrasound wave to the target tissue; receiving an ultrasound echo of the ultrasound wave returned from the target tissue; obtaining an elasticity image of the target tissue according to the ultrasound echo; and displaying the elasticity image;
  when the interference characteristic information does not meet the preset condition, stopping transmitting the ultrasound wave to the target tissue,
  wherein the interference characteristic information meeting the preset condition comprises: a maximum amplitude value or a maximum difference value of amplitude values of the interference characteristic waveform is not greater than a preset threshold, and the interference characteristic information not meeting the preset condition comprises: the maximum amplitude value or the maximum difference value of the amplitude values of the interference characteristic waveform is greater than the preset threshold.

12. The method of claim 11, wherein the interference characteristic information comprises at least one of an amplitude value of an ECG signal, an amplitude value of a respiratory wave signal and a displacement value of the target tissue.

13. The method of claim 12, wherein, the interference characteristic information is the amplitude value of the ECG signal, and after obtaining the interference characteristic information, the method further comprises:
determining whether the amplitude value of the ECG signal is not greater than a first preset threshold, and when the amplitude value of the ECG signal is not greater than the first preset threshold, transmitting the ultrasound wave to the target tissue; or
determining whether the amplitude value of the ECG signal is not greater than a first preset threshold and not less than a second preset threshold, and when the amplitude value of the ECG signal is not greater than the first preset threshold and not less than the second preset threshold, transmitting the ultrasound wave to the target tissue; or
determining a maximum amplitude value of the ECG signal from amplitude values of the ECG signal, determining whether the maximum amplitude value of the ECG signal is not greater than a third preset threshold, and when the maximum amplitude value of the ECG signal is not greater than the third preset threshold, transmitting the ultrasound wave to the target tissue; or
determining a maximum difference value of the amplitude values of the ECG signal according to the amplitude values of the ECG signal, determining whether the maximum difference value is not greater than a fourth preset threshold, and when the maximum difference value is not greater than the fourth preset threshold, transmitting the ultrasound wave to the target tissue; or
determining a maximum amplitude value of the ECG signal from the amplitude values of the ECG signal, determining a first time corresponding to the maximum amplitude value of the ECG signal, and transmitting the ultrasound wave to the target tissue at a second time that is at a preset time interval from the first time.

14. The method of claim 12, wherein, the interference characteristic information is the amplitude value of the respiratory wave signal, and after obtaining the interference characteristic information, the method further comprises:
determining whether the amplitude value of the respiratory wave signal is not greater than a first preset threshold, and when the amplitude value of the respiratory wave signal is not greater than the first preset threshold, transmitting the ultrasound wave to the target tissue; or
determining whether the amplitude value of the respiratory wave signal is not greater than a first preset threshold and not less than a second preset threshold, and when the amplitude value of the respiratory wave signal is not greater than the first preset threshold and not less than the second preset threshold, transmitting the ultrasound wave to the target tissue; or
determining a maximum amplitude value of the respiratory wave signal from amplitude values of the respiratory wave signal, determining whether the maximum amplitude value of the respiratory wave signal is not greater than a third preset threshold, and when the maximum amplitude value of the respiratory wave signal is not greater than the third preset threshold, transmitting the ultrasound wave to the target tissue; or
determining a maximum difference value of the amplitude values of the respiratory wave signal according to the amplitude values of the respiratory wave signal, determining whether the maximum difference value is not greater than a fourth preset threshold, and when the maximum difference value is not greater than the fourth preset threshold, transmitting the ultrasound wave to the target tissue; or
determining a maximum amplitude value of the respiratory wave signal from the amplitude values of the respiratory wave signal, determining a first time corresponding to the maximum amplitude value of the respiratory wave signal, and transmitting the ultrasound wave to the target tissue at a second time that is at a preset time interval from the first time.

15. The method of claim 12, wherein, the interference characteristic information is the displacement value of the target tissue, obtaining the interference characteristic information comprises:
obtaining a first ultrasound data of the target tissue at a first time;
obtaining a first position information of the target tissue according to the first ultrasound data;
obtaining a second ultrasound data of the target tissue at a second time;
obtaining a second position information of the target tissue according to the second ultrasound data; and
determining the displacement value of the target tissue according to the first position information and the second position information; and
after obtaining the interference characteristic information, the method further comprises:
determining whether the displacement value of the target tissue is not greater than a first preset threshold, and when the displacement value of the target tissue is not greater than the first preset threshold, transmitting the ultrasound wave to the target tissue; or
determining whether the displacement value of the target tissue is not greater than a first preset threshold and not less than a second preset threshold, and when the displacement value of the target tissue is not greater than the first preset threshold and not less than the second preset threshold, transmitting the ultrasound wave to the target tissue; or
determining a maximum displacement value of the target tissue from displacement values of the target tissue, determining whether the maximum displacement value of the target tissue is not greater than a third preset threshold, and when the maximum displacement value of the target tissue is not greater than the third preset threshold, transmitting the ultrasound wave to the target tissue; or
determining a maximum difference value of the displacement values of the target tissue according to the displacement values of the target tissue, determining whether the maximum difference value is not greater than a fourth preset threshold, and when the maximum difference value is not greater than the fourth preset threshold, transmitting the ultrasound wave to the target tissue; or
determining a maximum displacement value of the target tissue from the displacement values of the target tissue, determining a first time corresponding to the maximum displacement value of the target tissue, and transmitting the ultrasound wave to the target tissue at a second time that is at a preset time interval from the first time.

16. An elasticity imaging method, comprising:
performing an elasticity imaging on a target tissue to obtain an elasticity image of the target tissue;
obtaining an interference characteristic information, wherein the interference characteristic information represents a degree of interference to the target tissue;
displaying an interference characteristic waveform corresponding to the interference characteristic information;
determining whether the interference characteristic information meets a preset condition based on a degree of change in an amplitude value of the interference characteristic waveform;
when the interference characteristic information meets the preset condition, displaying the elasticity image; and
when the interference characteristic information does not meet the preset condition, stopping displaying the elasticity image,
wherein the interference characteristic information meeting the preset condition comprises: a maximum amplitude value or a maximum difference value of amplitude values of the interference characteristic waveform is not greater than a preset threshold, and the interference characteristic information not meeting the preset condition comprises: the maximum amplitude value or the maximum difference value of the amplitude values of the interference characteristic waveform is greater than the preset threshold.

17. The method of claim 16, wherein the interference characteristic information comprises at least one of an amplitude value of an ECG signal, an amplitude value of a respiratory wave signal and a displacement value of the target tissue.

18. The method of claim 17, wherein, the interference characteristic information is the amplitude value of the ECG signal, and after obtaining the interference characteristic information, the method further comprises:
determining whether the amplitude value of the ECG signal is not greater than a first preset threshold, and when the amplitude value of the ECG signal is greater than the first preset threshold, stopping displaying the elasticity image; or
determining whether the amplitude value of the ECG signal is not greater than a first preset threshold and not less than a second preset threshold, and when the amplitude value of the ECG signal is greater than the first preset threshold or less than the second preset threshold, stopping displaying the elasticity image; or
determining a maximum amplitude value of the ECG signal from amplitude values of the ECG signal, determining whether the maximum amplitude value of the ECG signal is not greater than a third preset threshold, and when the maximum amplitude value of the ECG signal is greater than the third preset threshold, stopping displaying the elasticity image; or
determining a maximum difference value of the amplitude values of the ECG signal according to the amplitude values of the ECG signal, determining whether the maximum difference value is not greater than a fourth preset threshold, and when the maximum difference value is greater than the fourth preset threshold, stopping displaying the elasticity image; or
determining a maximum amplitude value of the ECG signal from the amplitude values of the ECG signal, determining a first time corresponding to the maximum amplitude value of the ECG signal, and stopping displaying the elasticity image at a second time that is at a preset time interval from the first time.

19. The method of claim 17, wherein, the interference characteristic information is the amplitude value of the respiratory wave signal, and after obtaining the interference characteristic information, the method further comprises:
determining whether the amplitude value of the respiratory wave signal is not greater than a first preset threshold, and when the amplitude value of the respiratory wave signal is greater than the first preset threshold, stopping displaying the elasticity image; or
determining whether the amplitude value of the respiratory wave signal is not greater than a first preset threshold and not less than a second preset threshold, and when the amplitude value of the respiratory wave signal is greater than the first preset threshold or less than the second preset threshold, stopping displaying the elasticity image; or
determining a maximum amplitude value of the respiratory wave signal from amplitude values of the respiratory wave signal, determining whether the maximum amplitude value of the respiratory wave signal is not greater than a third preset threshold, and when the maximum amplitude value of the respiratory wave signal is greater than the third preset threshold, stopping displaying the elasticity image; or
determining a maximum difference value of the amplitude values of the respiratory wave signal according to the amplitude values of the respiratory wave signal, determining whether the maximum difference value is not greater than a fourth preset threshold, and when the maximum difference value is greater than the fourth preset threshold, stopping displaying the elasticity image; or
determining a maximum amplitude value of the respiratory wave signal from the amplitude values of the respiratory wave signal, determining a first time corresponding to the maximum amplitude value of the respiratory wave signal, and stopping displaying the elasticity image at a second time that is at a preset time interval from the first time.

20. The method of claim 17, wherein, the interference characteristic information is the displacement value of the target tissue, obtaining the interference characteristic information comprises:
obtaining a first ultrasound data of the target tissue at a first time;
obtaining a first position information of the target tissue according to the first ultrasound data;
obtaining a second ultrasound data of the target tissue at a second time;
obtaining a second position information of the target tissue according to the second ultrasound data; and
determining the displacement value of the target tissue according to the first position information and the second position information; and
after obtaining the interference characteristic information, the method further comprises:
determining whether the displacement value of the target tissue is not greater than a first preset threshold, and when the displacement value of the target tissue is greater than the first preset threshold, stopping displaying the elasticity image; or
determining whether the displacement value of the target tissue is not greater than a first preset threshold and not less than a second preset threshold, and when displacement value of the target tissue is greater than the first preset threshold or less than the second preset threshold, stopping displaying the elasticity image; or determining a maximum displacement value of the target tissue from displacement values of the target tissue, determining whether the maximum displacement value of the target tissue is not greater than a third preset threshold, and when the maximum displacement value of the target tissue is greater than the third preset threshold, stopping displaying the elasticity image; or determining a maximum difference value of the displacement values of the target tissue according to the displacement values of the target tissue, determining whether the maximum difference value is not greater than a fourth preset threshold, and when the maximum difference value is greater than the fourth preset threshold, stopping displaying the elasticity image; or determining a maximum displacement value of the target tissue from the displacement values of the target tissue, determining a first time corresponding to the maximum displacement value of the target tissue, and stopping displaying the elasticity image at a second time that is at a preset time interval from the first time.

* * * * *